(12) United States Patent
Belcher et al.

(10) Patent No.: US 7,960,721 B2
(45) Date of Patent: Jun. 14, 2011

(54) LIGHT EMITTING DEVICES MADE BY BIO-FABRICATION

(75) Inventors: Angela Belcher, Lexington, MA (US); Evelyn Hu, Goleta, CA (US); Xina Quan, Saratoga, CA (US); Hash Pakbaz, Hayward, CA (US)

(73) Assignee: Siluria Technologies, Inc., San Francisco, CA (US)

( * ) Notice: Subject to any disclaimer, the term of this patent is extended or adjusted under 35 U.S.C. 154(b) by 608 days.

(21) Appl. No.: 12/030,752

(22) Filed: Feb. 13, 2008

(65) Prior Publication Data

US 2010/0053928 A1  Mar. 4, 2010

Related U.S. Application Data

(63) Continuation-in-part of application No. 11/679,726, filed on Feb. 27, 2007.

(60) Provisional application No. 60/889,703, filed on Feb. 13, 2007, provisional application No. 60/801,792, filed on May 19, 2006.

(51) Int. Cl.
*H01L 31/042* (2006.01)

(52) U.S. Cl. .................... 257/40; 257/E51.023

(58) Field of Classification Search ........... 257/40, 257/97, E51.015, E51.018, E51.023
See application file for complete search history.

(56) References Cited

U.S. PATENT DOCUMENTS

| 6,713,173 | B2 | 3/2004 | Mayes et al. |
| 6,815,063 | B1 | 11/2004 | Mayes |
| 2003/0068900 | A1 | 4/2003 | Belcher et al. |
| 2003/0073104 | A1 | 4/2003 | Belcher et al. |
| 2003/0113714 | A1 | 6/2003 | Belcher et al. |
| 2003/0148380 | A1 | 8/2003 | Belcher |
| 2004/0118451 | A1 | 6/2004 | Walukiewicz et al. |
| 2004/0127640 | A1 | 7/2004 | Belcher et al. |
| 2005/0052129 | A1* | 3/2005 | Yamashita .................... 313/506 |
| 2005/0130258 | A1* | 6/2005 | Trent et al. ................... 435/68.1 |
| 2005/0158762 | A1 | 7/2005 | Donnelly et al. |
| 2005/0164515 | A9 | 7/2005 | Belcher et al. |
| 2006/0003387 | A1 | 1/2006 | Peelle et al. |
| 2006/0121346 | A1 | 6/2006 | Nam et al. |

FOREIGN PATENT DOCUMENTS

| WO | 2006/076027 A2 | 7/2006 |
| WO | 2006/123130 A1 | 11/2006 |
| WO | 2006/138538 A1 | 12/2006 |

OTHER PUBLICATIONS

Dieluweit et al., "Formation of a gold superlattice on an S-layer with square lattice symmetry," Supramolecular Science 5:15-19, 1998.

(Continued)

*Primary Examiner* — Thomas L Dickey
(74) *Attorney, Agent, or Firm* — Seed IP Law Group PLLC

(57) ABSTRACT

A light emitting device includes a substrate layer, a first injection contact positioned over the substrate layer, a first dielectric layer positioned over the first injection contact, a light emission layer positioned over the first dielectric layer, a second dielectric layer positioned over the light emission layer and a second injection contact positioned over the second dielectric layer. The light emission layer includes an organic template having binding sites for binding nanoparticles into an array. The wavelength of emitted light is dependent upon the size of the nanoparticles and the pitch of the array. The light emitting device may include a first plurality of binding sites for binding a first set of nanoparticles and a second plurality of binding sites for binding a second set of nanoparticles. The wavelength depends upon a ratio of the first plurality to the second plurality of binding sites.

46 Claims, 23 Drawing Sheets

OTHER PUBLICATIONS

Douglas and Young, "Virus Particles as Templates for Materials Synthesis," Adv Mater 11(8):679-681, 1999.

Douglas et al., "Protein Engineering of a Viral Cage for Constrained Nanomaterials Synthesis," Adv Mater 14(6):415-418, Mar. 18, 2002.

Flynn et al., "Viruses as vehicles for growth, organization and assembly of materials," Acta Materialia 51:5867-5880, 2003.

Flynn et al., "Synthesis and organization of nanoscale II-VI semiconductor materials using evolved peptide specificity and viral capsid assembly," J Mater Chem 13:2414-2421, 2003.

Hartgerink et al., "Peptide-amphiphile nanofibers: A versatile scaffold for the preparation of self-assembling materials," PNAS 99(8):5133-5138, Apr. 16, 2002.

Hoff et al., "Nanoscale Protein Patterning by Imprint Lithography," Nano Letters 4(5):853-857, 2004.

Huang et al., "Programmable Assembly of Nanoarchitectures Using Genetically Engineered Viruses," Nano Letters 5 (7):1429-1434, 2005.

Lee, A. and Subramanian, "Development of Nano-Composite Lead-Free Electronic Solders," J Electronic Materials 34(11):1399-1407, 2005.

Lee, S-W et al., "Ordering of Quantum Dots Using Genetically Engineered Viruses," Science 296:892-895, May 3, 2002.

Lee, S-K et al., "Cobalt Ion Mediated Self-Assembly of Genetically Engineered Bacteriophage for Biomimetic Co-Pt Hybrid Material," Biomacromolecules 7:14-17, 2006.

Mao et al., "Viral assembly of oriented quantum dot nanowires," PNAS 100(12):6946-6951, Jun. 10, 2003.

Mao et al., "Virus-Based Toolkit for the Directed Synthesis of Magnetic and Semiconducting Nanowires," Science 303:213-217, Jan. 9, 2004.

McMillan et al., "Ordered nanoparticle arrays formed on engineered chaperonin protein templates," Nature Materials 1:247-252, Dec. 2002.

Nam et al., "Genetically Driven Assembly of Nanorings Based on the M13 Virus," Nano Letters 0(0:A-E [undated].

Peelle et al., "Design Criteria for Engineering Inorganic Material-Specific Peptides," Langmuir 21(15):6929-6933, 2005.

Pum et al., "S-Layer proteins as basic building blocks in a biomolecular construction kit," Nanotechnology 11:100-107, 2000.

Reches and Gazit, "Casting Metal Nanowires Within Discrete Self-Assembled Peptide Nanotubes," Science 300:625-627, Apr. 25, 2003.

Reiss et al., "Biological Routes to Metal Alloy Ferromagnetic Nanostructures," Nano Letters 4(6):1127-1132, 2004.

Sara and Sleytr, "S-Layer Proteins," J Bacteriology 182(4):859-868, Feb. 2000.

Scheibel et al., "Conducting nanowires built by controlled self-assembly of amyloid fibers and selective metal deposition," PNAS 100(8):4527-4532, Apr. 15, 2003.

Shenton et al., "Synthesis of cadmium sulphide superlattices using self-assembled bacterial S-layers," Nature 389:585-587, Oct. 9, 1997.

Tai et al., "Processing and Creep Properties of Sn-Cu Composite Solders with Small Amounts of Nanosized Ag Reinforcement Additions," J Electronic Materials 34(11):1357-1362, 2005.

Tanabe et al., "YAG glass-ceramic phosphor for white LED (II): Luminescence characteristics," Proc of SPIE, 5941:594112-1-594112-6 [undated].

Wei et al., "Breakdown of the band-gap-common-cation rule: The origin of the small band gap of InN," Physical Review B 67:165209-1-165209-4, 2003.

Whaley et al, "Selection of peptides with semiconductor binding specificity for directed nanocrystal assembly," Nature 405:665-668, Jun. 8, 2000.

Wu et al., "Intermetallic Reactions in a Sn-20In-2.8Ag Solder Ball-Grid-Array Package with Au/Ni/Cu Pads," J Electronic Materials 34(11):1385-1390, 2005.

Yokoi et al., "Dynamic reassembly of peptide RADA16 nanofiber scaffold," PNAS 102(24):8414-8419, Jun. 14, 2005.

\* cited by examiner

Fig. 12.6. Bandgap energy and lattice constant of various III–V semiconductors at room temperature (adopted from Tien, 1988).

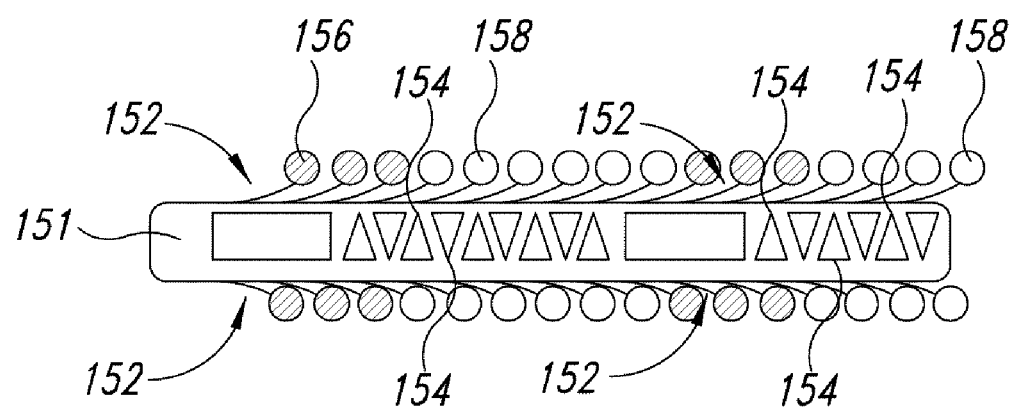
FIG. 7
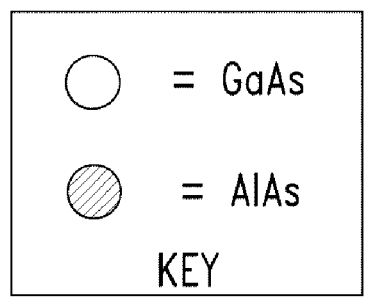

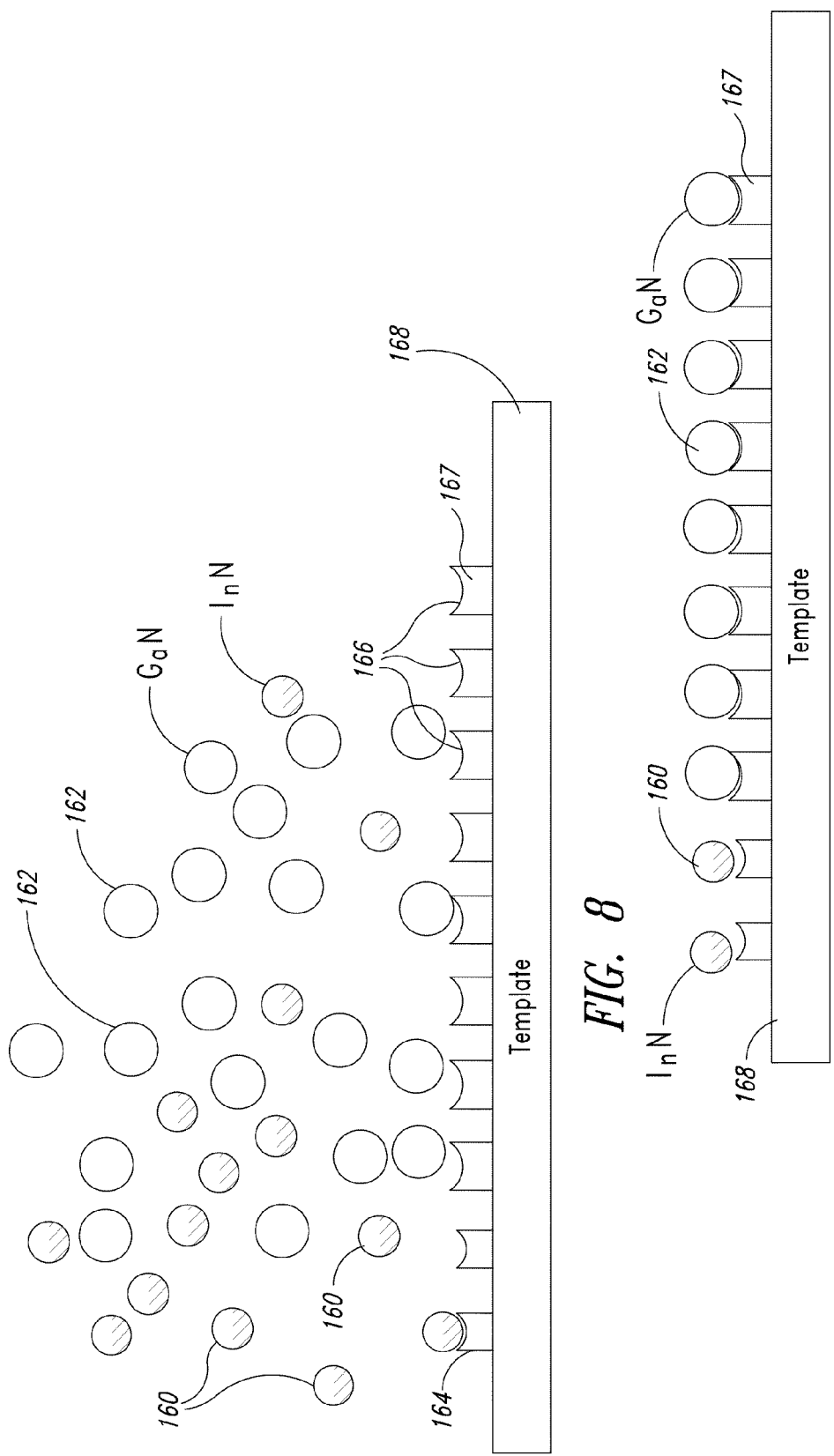

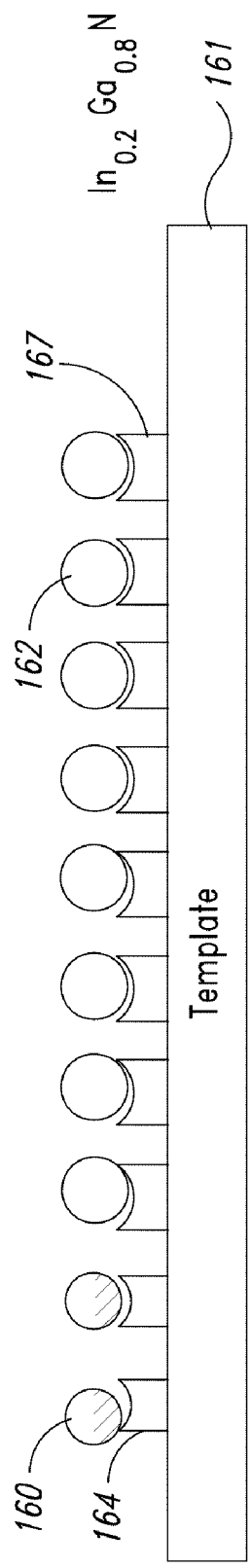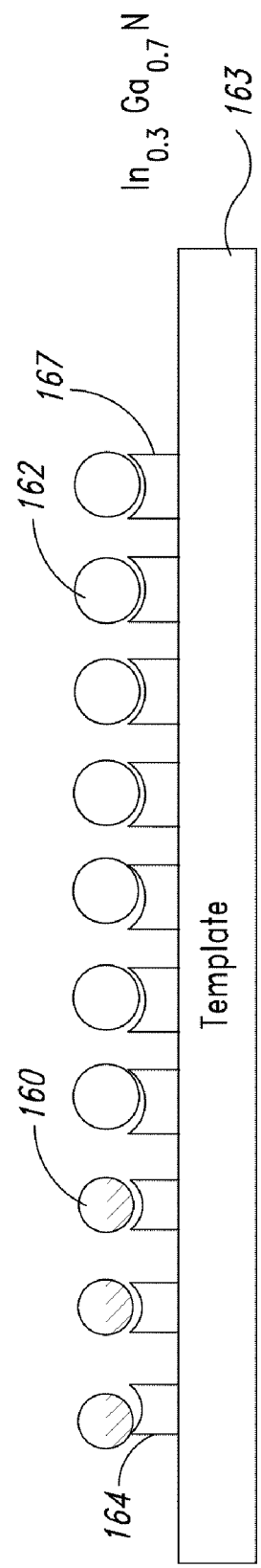

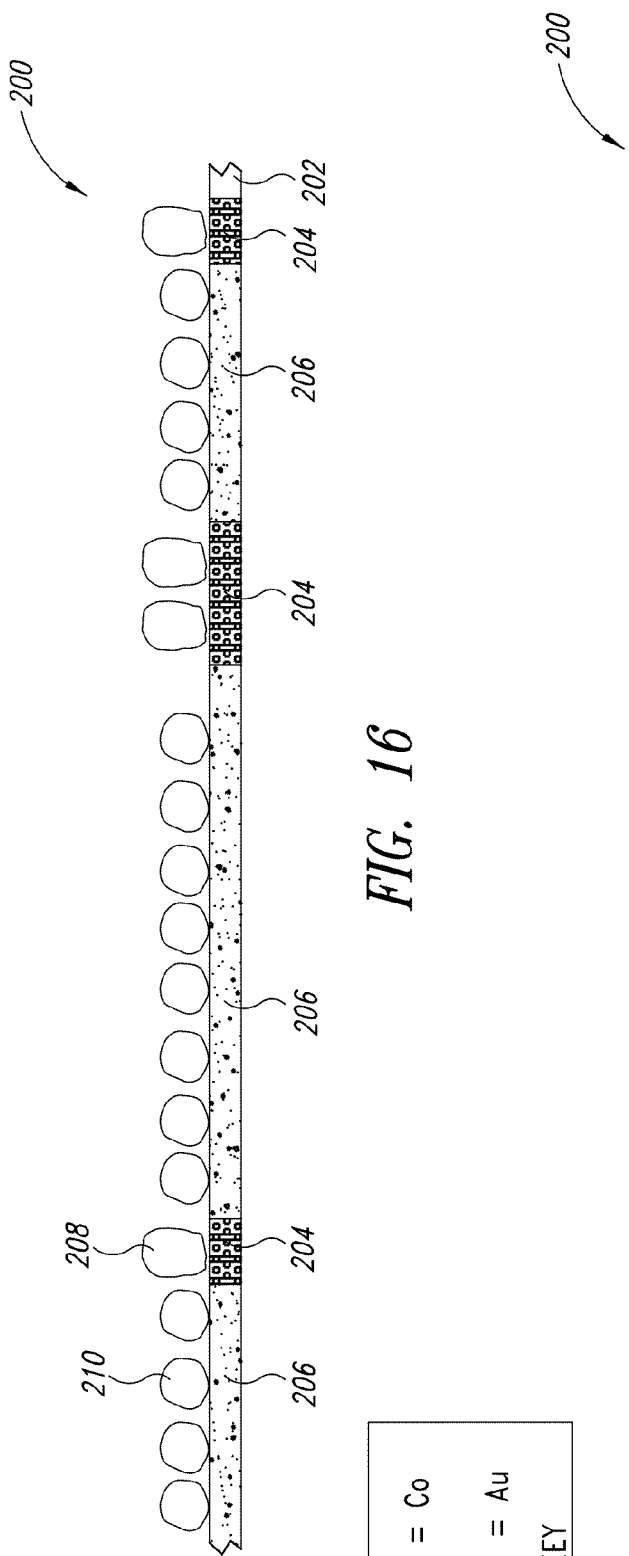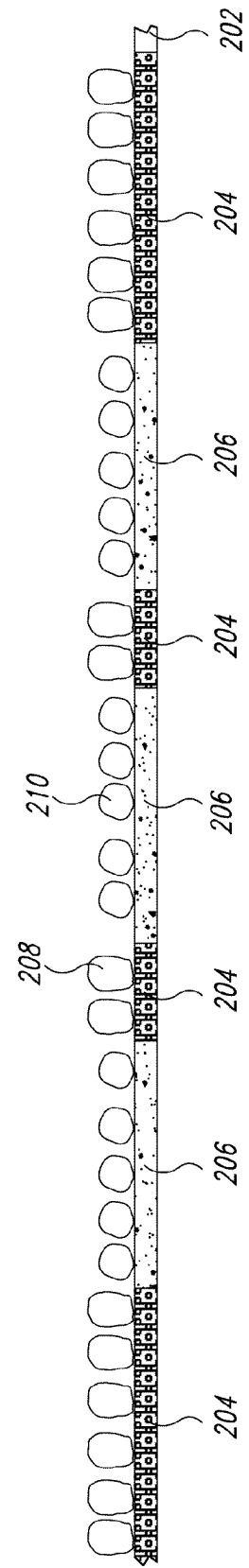
FIG. 16
FIG. 17

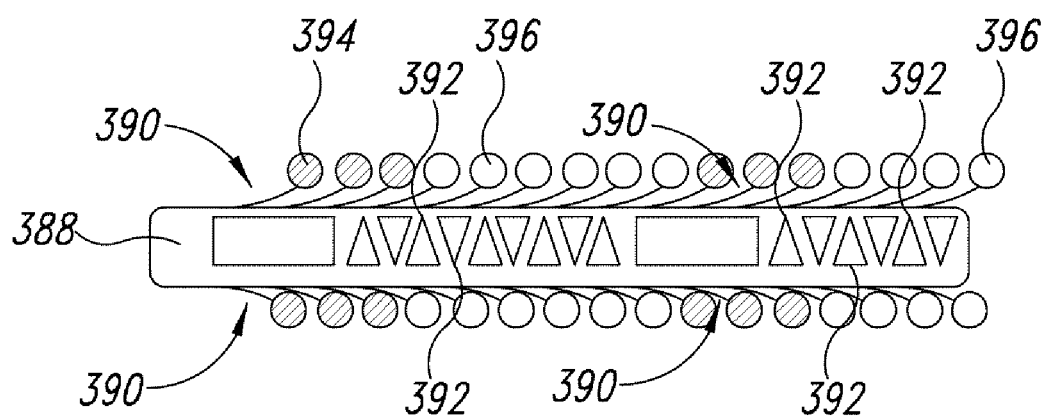
FIG. 26
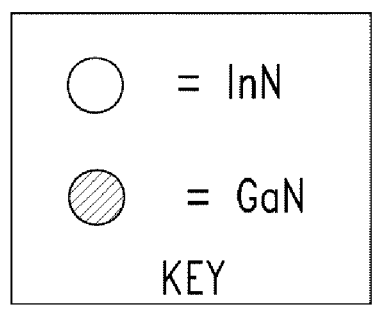
KEY

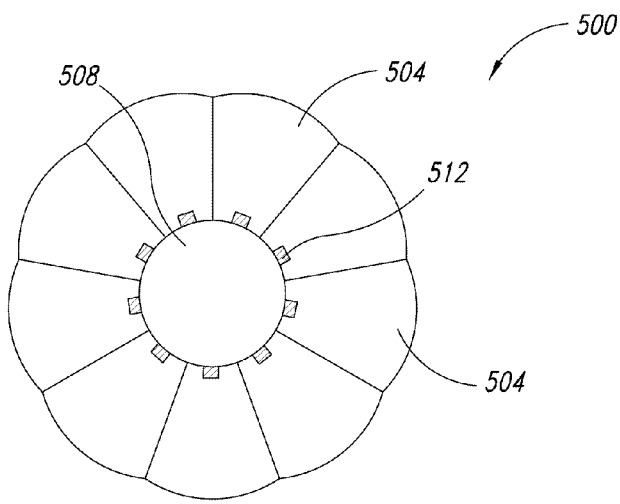
FIG. 30
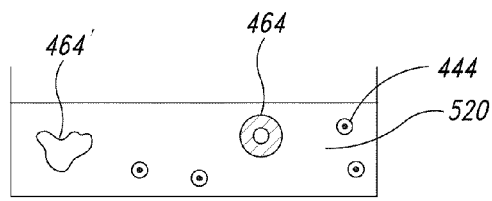
FIG. 31A
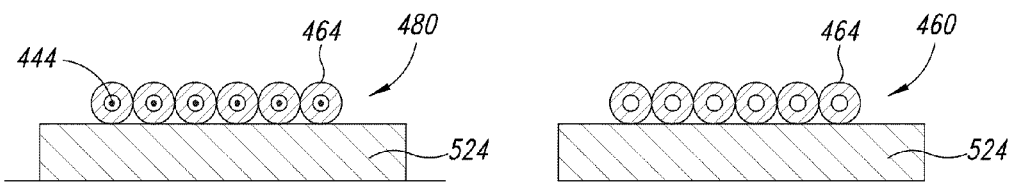
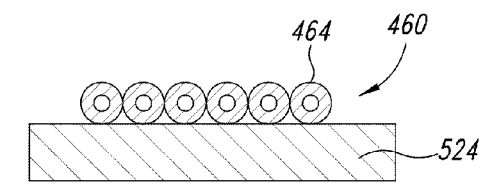
FIG. 32A
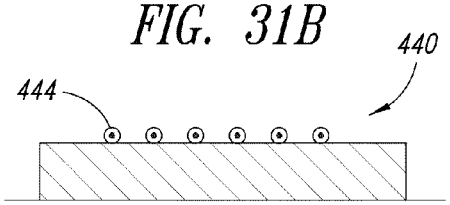
FIG. 31B
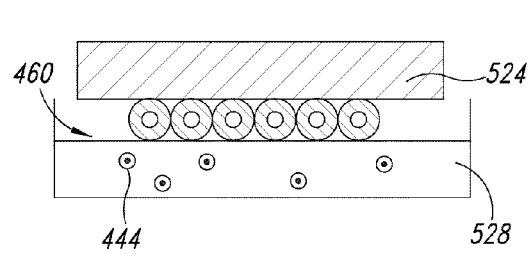
FIG. 31C
FIG. 32B

```
                        SEQUENCE LISTING

<160> NUMBER OF SEQ ID NOS: 25

<210> SEQ ID NO 1
<211> LENGTH: 16
<212> TYPE: PRT
<213> ORGANISM: Artificial Sequence
<220> FEATURE:
<223> OTHER INFORMATION: Suitable precursor protein that can convert or
      assemble into amyloid fibers.
<220> FEATURE:
<221> NAME/KEY: ACETYLATION
<222> LOCATION: 1

<400> SEQUENCE: 1

Arg Ala Asp Ala Arg Ala Asp Ala Arg Ala Asp Ala Arg Ala Asp Ala
 1               5                  10                  15

<210> SEQ ID NO 2
<211> LENGTH: 12
<212> TYPE: PRT
<213> ORGANISM: Artificial Sequence
<220> FEATURE:
<223> OTHER INFORMATION: Suitable precursor protein that can convert or
      assemble into amyloid fibers.
<220> FEATURE:
<221> NAME/KEY: MOD_RES
<222> LOCATION: 1
<223> OTHER INFORMATION: Biotin

<400> SEQUENCE: 2

Arg Gly Asp Ser Lys Gly Gly Gly Ala Ala Ala Lys
 1               5                  10

<210> SEQ ID NO 3
<211> LENGTH: 21
<212> TYPE: PRT
<213> ORGANISM: Artificial Sequence
<220> FEATURE:
<223> OTHER INFORMATION: Suitable precursor protein that can convert or
```

-continued assemble into amyloid fibers.

<400> SEQUENCE: 3

Trp Ser Trp Arg Ser Pro Thr Pro His Val Val Thr Asp Lys Gly Gly
1               5                   10                  15

Gly Ala Ala Ala Lys
            20

<210> SEQ ID NO 4
<211> LENGTH: 18
<212> TYPE: PRT
<213> ORGANISM: Artificial Sequence
<220> FEATURE:
<223> OTHER INFORMATION: Suitable precursor protein that can convert or
      assemble into amyloid fibers.

<400> SEQUENCE: 4

Ala Val Ser Gly Ser Ser Pro Asp Ser Lys Lys Gly Gly Gly Ala Ala
1               5                   10                  15

Ala Lys

<210> SEQ ID NO 5
<211> LENGTH: 9
<212> TYPE: PRT
<213> ORGANISM: unknown
<220> FEATURE:
<223> OTHER INFORMATION: Peptide sequences that have been identified to
      have specific affinity to a number of
      semiconductor and metallic materials.

<400> SEQUENCE: 5

Cys Asn Asn Pro Met His Gln Asn Cys
1               5

<210> SEQ ID NO 6
<211> LENGTH: 12
<212> TYPE: PRT
<213> ORGANISM: unknown
<220> FEATURE:
<223> OTHER INFORMATION: Peptide sequences that have been identified to
      have specific affinity to a number of
      semiconductor and metallic materials.

<400> SEQUENCE: 6

Leu Arg Arg Ser Ser Glu Ala His Asn Ser Ile Val
1               5                   10

<210> SEQ ID NO 7
<211> LENGTH: 9
<212> TYPE: PRT
<213> ORGANISM: unknown
<220> FEATURE:
<223> OTHER INFORMATION: Peptide sequences that have been identified to
      have specific affinity to a number of
      semiconductor and metallic materials.

<400> SEQUENCE: 7

Cys Thr Tyr Ser Arg Leu His Leu Cys
1               5

<210> SEQ ID NO 8
<211> LENGTH: 12
<212> TYPE: PRT
<213> ORGANISM: unknown
<220> FEATURE:
<223> OTHER INFORMATION: Peptide sequences that have been identified to
      have specific affinity to a number of
      semiconductor and metallic materials.

```
<400> SEQUENCE: 8

Ser Leu Thr Pro Leu Thr Thr Ser His Leu Arg Ser
1               5                   10

<210> SEQ ID NO 9
<211> LENGTH: 12
<212> TYPE: PRT
<213> ORGANISM: unknown
<220> FEATURE:
<223> OTHER INFORMATION: Peptide sequences that have been identified to
      have specific affinity to a number of
      semiconductor and metallic materials.

<400> SEQUENCE: 9

His Asn Lys His Leu Pro Ser Thr Gln Pro Leu Ala
1               5                   10

<210> SEQ ID NO 10
<211> LENGTH: 9
<212> TYPE: PRT
<213> ORGANISM: unknown
<220> FEATURE:
<223> OTHER INFORMATION: Peptide sequences that have been identified to
      have specific affinity to a number of
      semiconductor and metallic materials.

<400> SEQUENCE: 10

Cys Asn Ala Gly Asp His Ala Asn Cys
1               5

<210> SEQ ID NO 11
<211> LENGTH: 12
<212> TYPE: PRT
<213> ORGANISM: unknown
<220> FEATURE:
<223> OTHER INFORMATION: Peptide sequences that have been identified to
      have specific affinity to a number of
      semiconductor and metallic materials.

<400> SEQUENCE: 11

Ser Val Ser Val Gly Met Lys Pro Ser Pro Arg Pro
1               5                   10

<210> SEQ ID NO 12
<211> LENGTH: 12
<212> TYPE: PRT
<213> ORGANISM: unknown
<220> FEATURE:
<223> OTHER INFORMATION: Peptide sequences that have been identified to
      have specific affinity to a number of
      semiconductor and metallic materials.

<400> SEQUENCE: 12

Val Ile Ser Asn His Arg Glu Ser Ser Arg Pro Leu
1               5                   10

<210> SEQ ID NO 13
<211> LENGTH: 12
<212> TYPE: PRT
<213> ORGANISM: unknown
<220> FEATURE:
<223> OTHER INFORMATION: Peptide sequences that have been identified to
      have specific affinity to a number of
      semiconductor and metallic materials.

<400> SEQUENCE: 13

Lys Ser Leu Ser Arg His Asp His Ile His His His
1               5                   10
```

```
<210> SEQ ID NO 14
<211> LENGTH: 8
<212> TYPE: PRT
<213> ORGANISM: Unknown
<220> FEATURE:
<223> OTHER INFORMATION: Peptide sequences that have been identified to
      have specific affinity to a number of
      semiconductor and metallic materials.

<400> SEQUENCE: 14

Val Ser Gly Ser Ser Pro Asp Ser
 1               5

<210> SEQ ID NO 15
<211> LENGTH: 6
<212> TYPE: PRT
<213> ORGANISM: unknown
<220> FEATURE:
<223> OTHER INFORMATION: Peptide sequences that have been identified to
      have specific affinity to a number of
      semiconductor and metallic materials.

<400> SEQUENCE: 15

Ala Glu Glu Glu Glu Asp
 1               5

<210> SEQ ID NO 16
<211> LENGTH: 12
<212> TYPE: PRT
<213> ORGANISM: unknown
<220> FEATURE:
<223> OTHER INFORMATION: Peptide sequences that have been identified to
      have specific affinity to a number of
      semiconductor and metallic materials.

<400> SEQUENCE: 16

Lys Thr His Glu Ile His Ser Pro Leu Leu His Lys
 1               5                  10

<210> SEQ ID NO 17
<211> LENGTH: 8
<212> TYPE: PRT
<213> ORGANISM: unknown
<220> FEATURE:
<223> OTHER INFORMATION: Peptide sequences that have been identified to
      have specific affinity to a number of
      semiconductor and metallic materials.

<400> SEQUENCE: 17

Glu Pro Gly His Asp Ala Val Pro
 1               5

<210> SEQ ID NO 18
<211> LENGTH: 12
<212> TYPE: PRT
<213> ORGANISM: unknown
<220> FEATURE:
<223> OTHER INFORMATION: Peptide sequences that have been identified to
      have specific affinity to a number of
      semiconductor and metallic materials.

<400> SEQUENCE: 18

His Thr His Thr Asn Asn Asp Ser Pro Asn Gln Ala
 1               5                  10

<210> SEQ ID NO 19
<211> LENGTH: 15
<212> TYPE: PRT
```

-continued

```
<213> ORGANISM: unknown
<220> FEATURE:
<223> OTHER INFORMATION: Peptide sequences that have been identified to
      have specific affinity to a number of
      semiconductor and metallic materials.

<400> SEQUENCE: 19

Asp Val His His His Gly Arg His Gly Ala Glu His Ala Asp Ile
1               5                   10                  15

<210> SEQ ID NO 20
<211> LENGTH: 7
<212> TYPE: PRT
<213> ORGANISM: unknown
<220> FEATURE:
<223> OTHER INFORMATION: Peptide sequences that have been identified to
      have specific affinity to a number of
      semiconductor and metallic materials.

<400> SEQUENCE: 20

Lys His Lys His Trp His Trp
1               5

<210> SEQ ID NO 21
<211> LENGTH: 7
<212> TYPE: PRT
<213> ORGANISM: unknown
<220> FEATURE:
<223> OTHER INFORMATION: Peptide sequences that have been identified to
      have specific affinity to a number of
      semiconductor and metallic materials.

<400> SEQUENCE: 21

Arg Met Arg Met Lys Met Lys
1               5

<210> SEQ ID NO 22
<211> LENGTH: 7
<212> TYPE: PRT
<213> ORGANISM: unknown
<220> FEATURE:
<223> OTHER INFORMATION: Peptide sequences that have been identified to
      have specific affinity to a number of
      semiconductor and metallic materials.

<400> SEQUENCE: 22

Pro His Pro His Thr His Thr
1               5

<210> SEQ ID NO 23
<211> LENGTH: 9
<212> TYPE: PRT
<213> ORGANISM: unknown
<220> FEATURE:
<223> OTHER INFORMATION: Peptide sequences that have been identified to
      have specific affinity to a number of
      semiconductor and metallic materials.

<400> SEQUENCE: 23

Cys Ser Tyr His Arg Met Ala Thr Cys
1               5

<210> SEQ ID NO 24
<211> LENGTH: 9
<212> TYPE: PRT
<213> ORGANISM: unknown
<220> FEATURE:
<223> OTHER INFORMATION: Peptide sequences that have been identified to
      have specific affinity to a number of
      semiconductor and metallic materials.
```

```
<400> SEQUENCE: 24

Cys Thr Ser Pro His Thr Arg Ala Cys
1               5

<210> SEQ ID NO 25
<211> LENGTH: 12
<212> TYPE: PRT
<213> ORGANISM: unknown
<220> FEATURE:
<223> OTHER INFORMATION: Peptide sequences that have been identified to
      have specific affinity to a number of
      semiconductor and metallic materials.

<400> SEQUENCE: 25

Leu Lys Ala His Leu Pro Pro Ser Arg Leu Pro Ser
1               5                   10
```

LIGHT EMITTING DEVICES MADE BY BIO-FABRICATION

CROSS-REFERENCE TO RELATED APPLICATION

This application is a continuation-in-part of U.S. patent application Ser. No. 11/679,726, filed Feb. 27, 2007, which claims the benefit under 35 U.S.C. §119(e) of U.S. Provisional Patent Application No. 60/801,792, filed May 19, 2006.

This application also claims the benefit under 35 U.S.C. §119(e) of U.S. Provisional Patent Application No. 60/889,703, filed Feb. 13, 2007, where these applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 860158_413_SEQ_LISTING.txt. The text file is 8 KB, was created on Feb. 13, 2008, and is being submitted electronically via EFS-Web.

BACKGROUND

1. Technical Field

This application relates to nanoparticle-based light emitting devices formed by bio-fabrication, and in particular, to a system and manufacture of light-emitting device having a light emission layer formed of a semiconductor alloy.

2. Description of the Related Art

Optoelectronic devices include a wide range of electrical-to-optical, or optical-to-electrical transducers, such as photodiodes (including solar cells), phototransistors, light-dependent resistors, lasers, light-emitting diodes (LED), fiber optics and the like. Regardless of the type, an optoelectronic device operates based on at least one of two fundamental processes, namely, creating electron-hole pairs by photon absorption, or emitting photons by recombining electrons and holes.

Semiconductor materials have unique electronic band structures, which can be impacted by the quantum mechanical effect of light. They are thus materials of choice in fabricating optoelectronic devices. In a semiconductor material, the uppermost-occupied band is typically completely filled and is referred to as a valence band; whereas the lowest unoccupied band is referred to as a conduction band. Electrons in the valence band can absorb photon energy and be excited to the conduction band, leaving holes in the valence band. The semiconductor material becomes conductive when an appreciable number of electrons are present in the conduction band. Conversely, electrons in the conduction band can be recombined with a hole in the valence band and cause spontaneous or stimulated emission of photons.

The optical and electrical properties of a semiconductor material are largely determined by the energy difference ("band gap") between its valence band and conduction band. For example, during the process of creating electron-hole pairs, the bandgap is a direct measure of the minimum photon energy required to excite an electron from the valence band to the conduction band. When an electron and hole recombine, the bandgap determines the photon energy emitted. Accordingly, controlling the bandgap is an effective way of controlling the optical and electrical properties and outputs of the optoelectronic devices.

The bandgap is an intrinsic property of a given semiconductor material. Bandgaps can be adjusted by doping a semiconductor material with an impurity according to known methods. Alternatively, semiconductor alloys formed by two or more semiconductor components have been created. The bandgap of such an alloy is different from that of the semiconductor components, and is typically a function of the bandgaps and the relative amounts of the components.

Generally speaking, in creating a new alloy, two or more elements are allowed to grow into one crystal lattice. More commonly, two types of binary alloys (e.g., AlAs, InP, GaAs and the like) are grown into a tertiary or quaternary alloy. Lattice match of the components is therefore important in reducing the strain and defects of the resulting alloy.

FIG. 1 shows the bandgap energies (eV) and lattice constants of various Group III-V semiconductors. As illustrated, two binary semiconductor alloys, AlAs and GaAs, have nearly identical lattice constants (about 5.65). Their bandgaps are respectively 2.20 eV and 1.42 eV. Because of the matching lattice constants, AlAs and GaAs are suitable to form a relatively stable tertiary alloy, which can be represented by $Al_xGa_{1-x}As$ (x being the atomic percentage of AlAs in the alloy). The bandgap of the tertiary alloy is a function of x as well as the bandgaps of the pure AlAs and GaAs. This example illustrates an approach to engineering bandgaps by controlling the compositions of semiconductor alloys.

Controlling the composition of an alloy shows promise for creating new materials with tunable optoelectrical or mechanical properties. Currently, semiconductor alloys such as $Al_xGa_{1-x}As$, $In_xGa_{1-x}N$ and $Al_xGa_{1-x}N$ are fabricated by epitaxial growth techniques such as Metal Organic Chemical Vapor Deposition (MOCVD) or Molecular Beam Epitaxy (MBE). However, technical challenges remain in growing these epitaxial layers, in spite of the relative strain-tolerance and defect-tolerance of the materials. In particular, their mechanical stability and integrity are difficult to maintain due to strain, which, in turn, limits the thickness of the layers grown. The compositional control is also influenced by the strain in the material.

Some semiconductor materials do not have an acceptable lattice match that will permit them to be formed in a stable compound or heterostructure using standard bulk crystal or epitaxial growth techniques. Thus, engineering a specific bandgap or having a particular alloy composition is very difficult and sometimes not possible with current semiconductor technology

BRIEF SUMMARY

In one embodiment, a light emitting device for emitting light includes a substrate layer, a first injection contact positioned over the substrate layer, a first dielectric layer positioned over the first injection contact, a light emission layer positioned over the first dielectric layer, a second dielectric layer positioned over the light emission layer and a second injection contact positioned over the second dielectric layer. The light emission layer includes a nanoparticle layer, wherein the nanoparticle layer comprises an organic template having a plurality of binding sites for binding a plurality of nanoparticles into the nanoparticle layer;

Furthermore, the wavelength of emitted light is dependent upon the size of the nanoparticles and the pitch of the nanoparticle array. In one embodiment, the nanoparticle size is selected from a range of preferably 1 to 100 nanometers and more preferably 1-10 nanometers. In another embodiment, the pitch of the array is selected from a range of preferably 1 to 100 nanometers and more preferably 1-10 nanometers.

In one embodiment, the light emitting device includes a first plurality of binding sites configured for binding a first set of nanoparticles of binary composition AB and a second plurality of binding sites configured for binding a second set of nanoparticles of binary composition CD, where A is a first element, B is a second element, C is a third element and D is a fourth element. The wavelength of emitted light depends upon a ratio of the first plurality of binding sites to the second plurality of binding sites.

In another embodiment, the organic template includes a first plurality of binding sites with an affinity for a first selected binary nanoparticle and a second plurality of binding sites with an affinity for a second selected binary nanoparticle. In yet another embodiment, the organic template is a peptide having first binding sites for the first binary nanoparticle located at positions along the peptide and second binding sites for the second binary nanoparticle located at other positions along the peptide.

According to one embodiment, a method of emitting light from a plurality of nanoparticles which form a nanoparticle array includes selecting characteristics of the nanoparticle array, injecting electrons into the plurality of nanoparticles, injecting holes into the plurality of nanoparticles, and generating light of a wavelength based upon the selected characteristics. An organic template binds the nanoparticles to form the nanoparticle array. Generating light of a specific wavelength includes selecting a size of the nanoparticles and a pitch of the nanoparticle array. Selecting larger nanoparticles generates light of a longer wavelength. Selecting larger nanoparticle array pitches generates light of a shorter wavelength.

In one embodiment, the wavelength depends upon selecting a composition of the plurality of nanoparticles that form the nanoparticle array. Selecting a composition of the plurality of nanoparticles includes determining a first plurality of binding sites on the organic template for binding a first plurality of nanoparticles of binary composition AB, and determining a second plurality of binding sites on the organic template for binding a second plurality of nanoparticles of binary composition CD, where A is a first element, B is a second element, C is a third element and D is a fourth element. In one embodiment, the wavelength of the generated light depends upon a ratio of the first plurality of binding sites to the second plurality of binding sites.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been selected solely for ease of recognition in the drawings.

FIG. 7 illustrates a template for achieving a ternary compound bandgap using only binary components.

FIG. 8 illustrates a template having engineered binding sites at a selected ratio for specific nanoparticles according to one embodiment.

FIG. 9 illustrates the nanoparticles coupled to the respective binding sites of the template of FIG. 8.

FIG. 10 illustrates a first ratio of binding sites for binary components to emulate a selected ternary compound.

FIG. 11 illustrates a different ratio of the same binding sites to emulate a different ternary compound.

FIG. 16 illustrates a template having a selected ratio of binding sites for elements to emulate a specific compound.

FIG. 17 illustrates a template for the same elements, having a different ratio of binding sites to emulate a different compound.

FIG. 26 illustrates a template that has been engineered having the desired ratio of a material that emulates a ternary compound of $Ga_xIn_{1-x}N$.

FIG. 30 illustrates a chaperonin having an outside surface, a top surface and an inside surface.

FIG. 31A illustrates a fluid suspension of nanoparticles and lattices.

FIG. 31B illustrates a structure with templates bound to nanoparticles.

FIG. 31C illustrates a nanoparticle array with the templates removed.

FIG. 32A illustrates an ordered structure of templates.

FIG. 32B illustrates the ordered structure of FIG. 32A in contact with a suspension of nanoparticles.

DETAILED DESCRIPTION

Alloys with precision-controlled compositions are described. These alloys, also referred to herein as "digital alloys," are hybrids of two or more types of nanostructure components (e.g., "nanocrystals"), which are assembled in the presence of templates. As will be described further in detail, a nanostructure component is a nanoscale building block and can be an elemental material (including a single element) or a binary (including two elements) material. The templates are biological or non-biological scaffolds including binding sites that specifically bind to selected nanocrystals, and where the binding sites are separated by distances on the order of nanometers or 10's of nanometers. The composition of the digital alloy is determined by the nanocrystal components at a stoichiometry controlled by the distribution of the binding sites.

Due to the small dimensions of the nanocrystals (typically only a few atoms) and their proximity to each other (typically a few nanometers to tens of nanometers), electrons cannot distinguish one nanocrystal component from another nanocrystal component as discrete materials. Instead, the electron behavior averages over the two or more different materials in the nanocrystals and perceives them as a single alloy. Thus, new materials of tunable macroscopic properties can be created by manipulating the nanoscale components.

Figure 2:
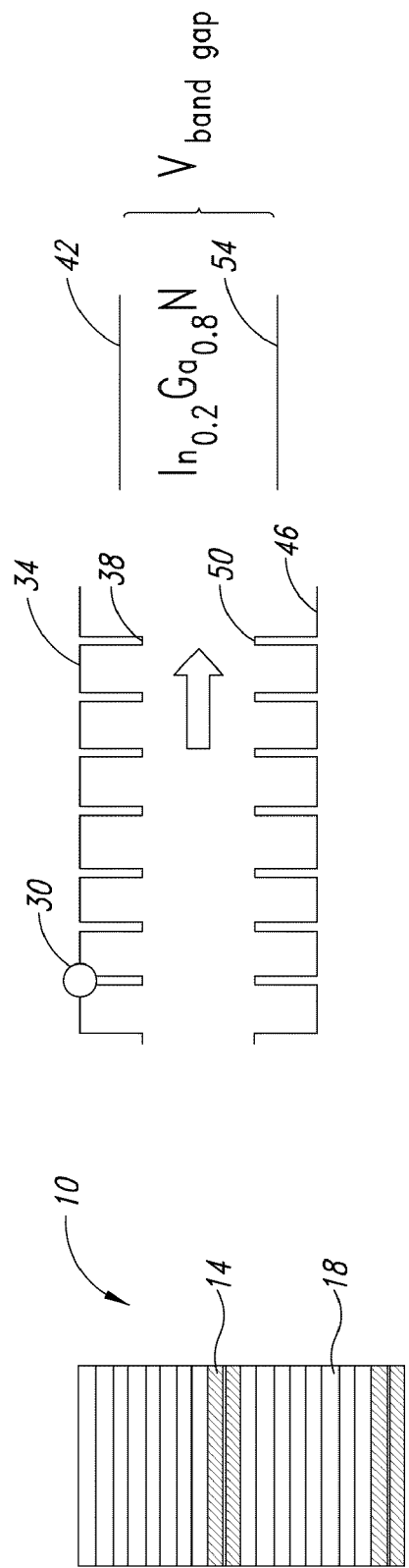
FIGS. 2A and 2B show schematically a digital alloy and the resulting bandgap according to one embodiment.

FIG. 2A shows schematically a digital alloy 10 made up of thin layers of two types of binary nanocrystals, 20% of a first binary nanocrystal 14 (e.g., InN) and 80% of a second nanocrystal 18 (e.g., GaN). FIG. 2B illustrates how an electron 30 perceives the digital alloy 10. From an electron's point of view, the conduction bands 34 of GaN and the conduction band 38 of InN are averaged to obtain a conduction band 42 of the digital alloy, which may be represented by $In_{0.2}Ga_{0.8}N$. Similarly, the valence bands of GaN 46 and the valence band 50 of InN are averaged out to obtain a valence band 54 of the alloy corresponding to $In_{0.2}Ga_{0.8}N$. The bandgap energy of the digital alloy is thus a value between the bandgap energies of the pure InN and GaN. In other words, electrons perceive the alloy 10 as a ternary alloy of a new composition ($In_{0.2}Ga_{0.8}N$), not as being two separate binary components InN and GaN. As will be described in detail below, the stoichiometry of each element in the new composition is controlled by using templates that are designed to bind to the two binary components at a selected ratio (e.g., 20%:80% for InN and GaN in FIG. 2A). The bandgap for this ternary alloy is a function of the stoichiometry of the individual components.

Macroscopically speaking, the assembled nanocrystal components emulate a new bulk material that has averaged properties of that of the component materials. These digital alloys therefore correspond to a wide range of optical, electrical and mechanical properties, which are typically unattainable in naturally occurring materials. For example, two layers of indium gallium nitride (InGaN), one tuned to a bandgap of 1.7 eV and the other to 1.1 eV, could attain the theoretical 50% maximum efficiency for a two-layer multijunction cell. Epitaxial growth of InGaN with a high % of In is currently difficult to achieve without material inhomogeneities and low optical efficiency. Currently, materials with specifically designed and selected bandgaps are often difficult to construct, however according to the methods described herein, such layers can be easily constructed having any selected bandgap, if the binary nanostructures are available.

Thus, certain embodiments are directed to an alloy comprising: a plurality of templates, each template including at least one first binding sites and at least one second binding sites, the first binding site having a specific binding affinity for a first nanoparticle of a first material, the second binding site having a specific binding affinity for a second nanoparticle of a second material, the templates are selected to include, in percentages, x first binding sites and y second binding sites; a plurality of the first nanocrystals bound to respective first binding sites; a plurality of the second nanocrystals bound to respective second binding sites; wherein the templates are assembled such that the first material and the second material form an alloy of the first material and the second material at a stoichiometric ratio of x:y.

Figure 3:
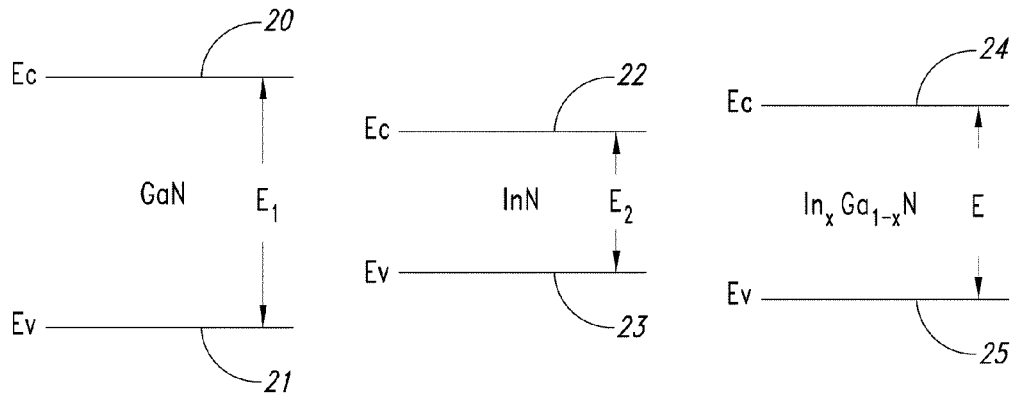
FIG. 3 shows an engineered bandgap according to one embodiment.

FIG. 3 illustrates the engineering of a desired bandgap according to a compositional control of a digital alloy. As used herein, the term "digital alloy" refers to combinations of any materials, including semiconductors, metals, metal oxides and insulators. As shown in FIG. 3, a first material (e.g., GaN) has a conduction band 20 and a valence band 21. The distance E1 between the conduction band 20 and the valence band 21 is the bandgap. For insulators, the bandgap is usually higher than 3 eV and cannot be overcome by electrons in the valence band, whereas for metallic conductors, there is no bandgap and the valence band overlaps the conduction band. In semiconductors, as described above, the bandgap is sufficiently small that electrons in the valence band can overcome the bandgap and be excited to the conduction band under certain conditions. FIG. 3 also illustrates the bandgap of a second material, (e.g., InN), having a conduction band 22 and a valence band 23, and therefore having a bandgap represented by the distance E2 between the two bands. A template is created having first binding sites and second binding sites in a user-designed and selected ratio (x:y), x and y being the percentages of the first and second binding sites and x+y is 1. The first and second binding sites are selected to bind to first and second materials, respectively. The ratio of the first material and the second material on the template is therefore in a stoichiometric ratio of x:y. The resulting digital alloy, as made from the two components (e.g., $In_xGa_yN$ or $In_xGa_{1-x}N$), will therefore have a valence band 25, a conduction band 24, and an engineerable bandgap E based on the identities and the stoichiometry of the two components.

As used herein, x and y can be represented by proper fractions or percentages (0<x<1, 0<y<1). For instance, in a two-component alloy (i.e., x+y=1), if the first binding site is present at x=20% of the combined first binding sites and second binding sites, it is understood that x can also be represented as a proper fraction 0.2. Moreover, a selected ratio of the first binding sites and second binding sites can be represented by x:y, this ratio corresponds to the stoichiometric ratio of the two materials made up the resulting alloy.

Figure 4A:
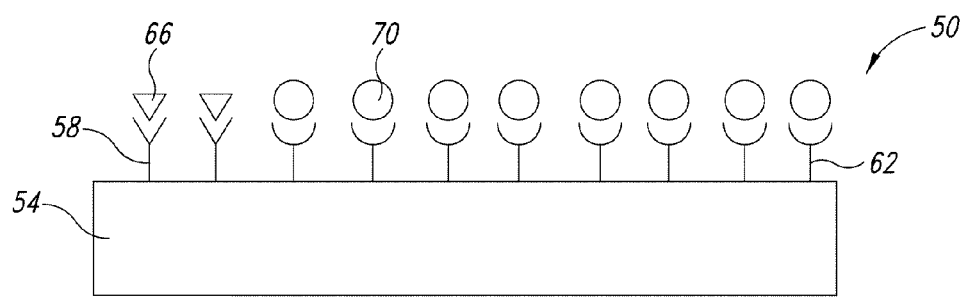
FIGS. 4A and 4B illustrate schematically a template and binding sites according to different embodiments.

FIG. 4A illustrates a template 50 comprising a scaffold 54 including first binding sites 58 and second binding sites 62 at a selected ratio of 20%:80%. The first binding sites 58 are coupled to first nanocrystals 66 with specificity, and the second binding sites 62 are coupled to second nanocrystals 70 with specificity. Thus, if the first nanocrystals are InN and the second nanocrystals are GaN, the resulting alloy formed by assembling the templates 50 can be represented by $In_{0.2}Ga_{0.8}N$.

Figure 4B:
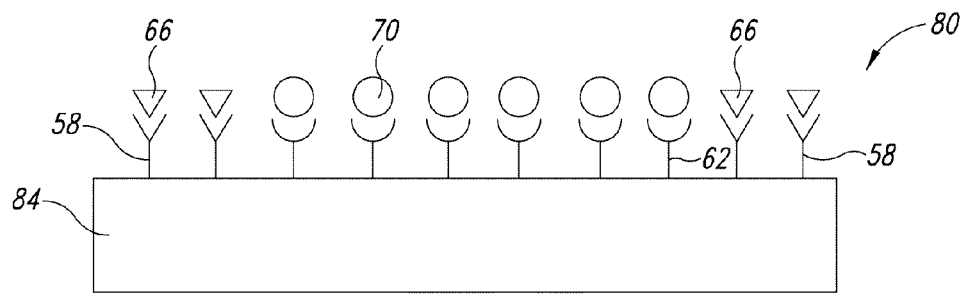

FIG. 4B illustrates another template 80 comprising the scaffold 84 including first binding sites 58 and second binding sites 62 at a selected ratio of 40%:60%. As will be discussed in more detail below, the same types of binding sites and the same corresponding nanocrystals as those illustrated in FIG. 4A can be used. However, the selected ratio of the first binding sites and the second binding sites are tuned to 40%:60%. Thus, if the first nanocrystals are InN and the second nanocrystals are GaN, the resulting alloy formed by assembling the templates 80 can be represented by $In_{0.4}Ga_{0.6}N$.

Thus, alloys can be synthesized in a controllable fashion using appropriate templates, in particular, by selecting a ratio of binding sites that correspond to different nanocrystal components. The resulting alloy, which is made up by nanoscale building blocks of two or more different materials, is not constrained by lattice match or geometries thereof. Physical properties, such as optical, electrical, magnetic and mechanical properties that are innately associated with a given composition of alloy, will be averaged over those of the nanocrystal components. Depending on the desired end use, semiconductor alloys and metallic alloys can be prepared based on semiconductor nanocrystals and metallic nanocrystals, respectively, as explained later herein.

A. Templates

"Templates" can be any synthetic and natural materials that provide binding sites to which nanocrystals can be coupled. As used herein, the templates are selected such that precision control of the binding sites, in terms of their composition, quantity and location can be achieved in a statistically significant manner. Both biological and non-biological based templates can be used.

Because peptides sequences have been demonstrated to have specific and selective binding affinity for many different types of nanocrystals, biological templates incorporating peptide sequences as binding sites are preferred. Moreover, biological templates can be engineered to comprise pre-determined binding sites in pre-determined spatial relationships (e.g., separated by a few to tens of nanometers). They are particularly advantageous for controlling the compositions of digital alloys. Biological templates include, for example, biomolecules and biological scaffold fused with peptide sequences.

As will be described in more detail below, biological templates can be manipulated through genetic engineering to generate specific binding sites at controllable locations on the templates. Non-biological templates can also be manipulated through precision patterning of binding sites at nanoscale resolutions.

1. Biological Templates:

As noted above, biological templates such as proteins and biological scaffolds can be engineered based on genetics to ensure control over the type of binding sites (e.g., peptide sequences), their locations on the templates and their respective density and/or ratio to other binding sites. See, e.g., Mao, C. B. et al., (2004) *Science* 303: 213-217; Belcher, A. et al., (2002) *Science* 296: 892-895; Belcher, A. et al., (2000) *Nature* 405 (6787) 665-668; Reiss et al., (2004) *Nanoletters*, 4 (6), 1127-1132, Flynn, C. et al., (2003) *J. Mater. Sci.*, 13, 2414-2421; Mao, C. B. et al., (2003) *PNAS*, 100 (12), 6946-6951, which references are hereby incorporated by reference in their entireties. Advantageously, this allows for the ability to control the composition and distribution of the binding sites on the biological template.

In certain embodiments, the biological template comprises, in percentages, x first peptide sequences and y second peptide sequences. Because of the specific affinity of the first peptide sequence for a first nanocrystal of a first material, and the second peptide sequence for a second nanocrystal of a second material, an alloy of the first material and the second material can be formed. More specifically, the alloy comprises the first material and the second material in a selected stoichiometry (x:y) determined by the relative amounts of the first binding sites and the second binding sites.

In other embodiments, it is not necessary that both the first binding sites and the second binding sites are present on a single type of template. Instead, the first binding sites may be present exclusively on a first type of template, and the second binding sites on a second type of template. The relative percentage of the first binding sites and second binding sites (x:y) can be controlled by a selected ratio of the first type of template and the second type of templates in the alloy composition.

a. Biomolecules

In certain embodiments, the biological templates are biomolecules such as proteins. "Biomolecule" refers to any organic molecule of a biological origin. Typically, a biomolecule comprises a plurality of subunits (building blocks) joined together in a sequence via chemical bonds. Each subunit comprises at least two reactive groups such as hydroxyl, carboxylic and amino groups, which enable the bond formations that interconnect the subunits. Examples of the subunits include, but are not limited to: amino acids (both natural and synthetic) and nucleotides. Examples of biomolecules include peptides, proteins (including cytokines, growth factors, etc.), nucleic acids and polynucleotides. A "peptide sequence" refers to two or more amino acids joined by peptide (amide) bonds. The amino-acid building blocks (subunits) include naturally occurring α-amino acids and/or unnatural amino acids, such as β-amino acids and homoamino acids. Moreover, an unnatural amino acid can be a chemically modified form of a natural amino acid. "Protein" refers to a natural or engineered macromolecule having a primary structure characterized by peptide sequences. In addition to the primary structure, the proteins also exhibit secondary and tertiary structures that determine their final geometric shapes.

Because protein synthesis can be genetically directed, they can be readily manipulated and functionalized to contain desired peptide sequences (i.e., binding sites) at desired locations within the primary structure of the protein. The protein can then be assembled to provide a template.

Thus, in various embodiments, the templates are biomolecules comprising at least one first peptide sequence and at least one second peptide sequence. In one embodiment, the templates are native proteins or proteins that can be engineered to have binding affinities for nanocrystals of at least two specific materials.

In certain embodiments, the biological templates are chaperonins, which can be engineered to have a binding affinity for a particular type of nanoparticle and which can self assemble into fibrils or ordered 2-d arrays (see, e.g., U.S. Patent Application 2005/0158762). Chaperonins are a type of proteins that readily self-assemble into many different shapes, including double-ring structures and form a crystalline array on a solid surface. Typically, adenosine triphosphate (ATP) and $Mg^{2+}$ are needed to mediate the crystallization. See, e.g. U.S. Patent Application 2005/0158762. Examples of how digital alloys can be formed from chaperoning are shown in FIGS. 5A, 5B, and 6.

Figure 5A:
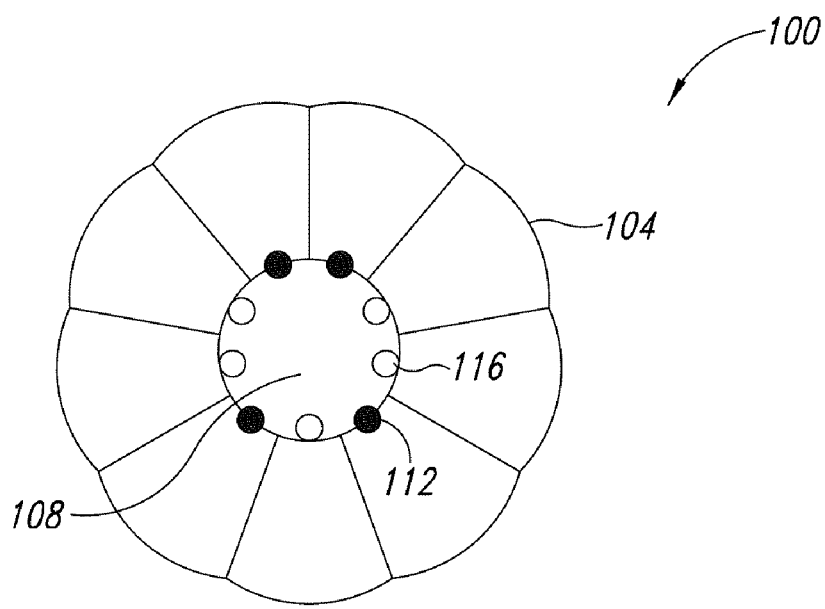
FIGS. 5A and 5B illustrate schematically different chaperonins according to various embodiments.
Figure 5B:
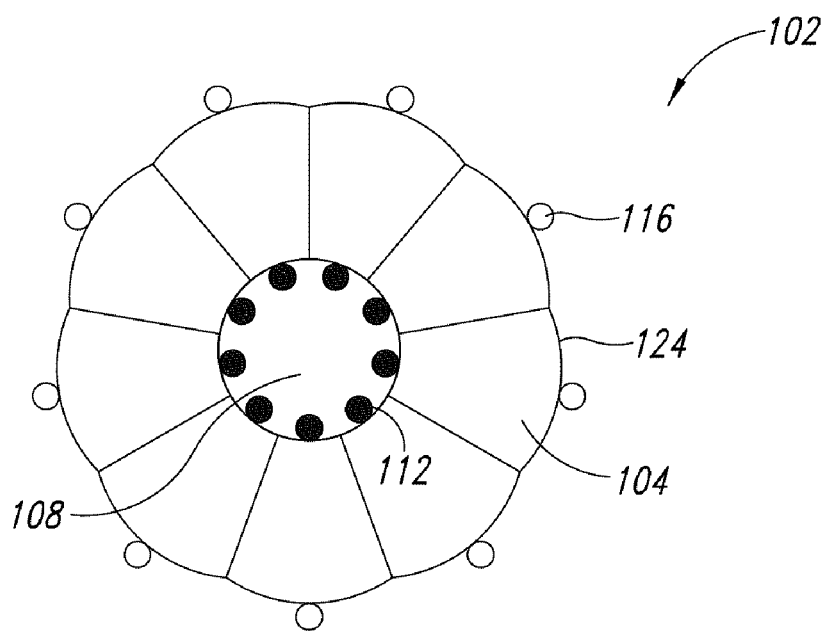
Figure 6:
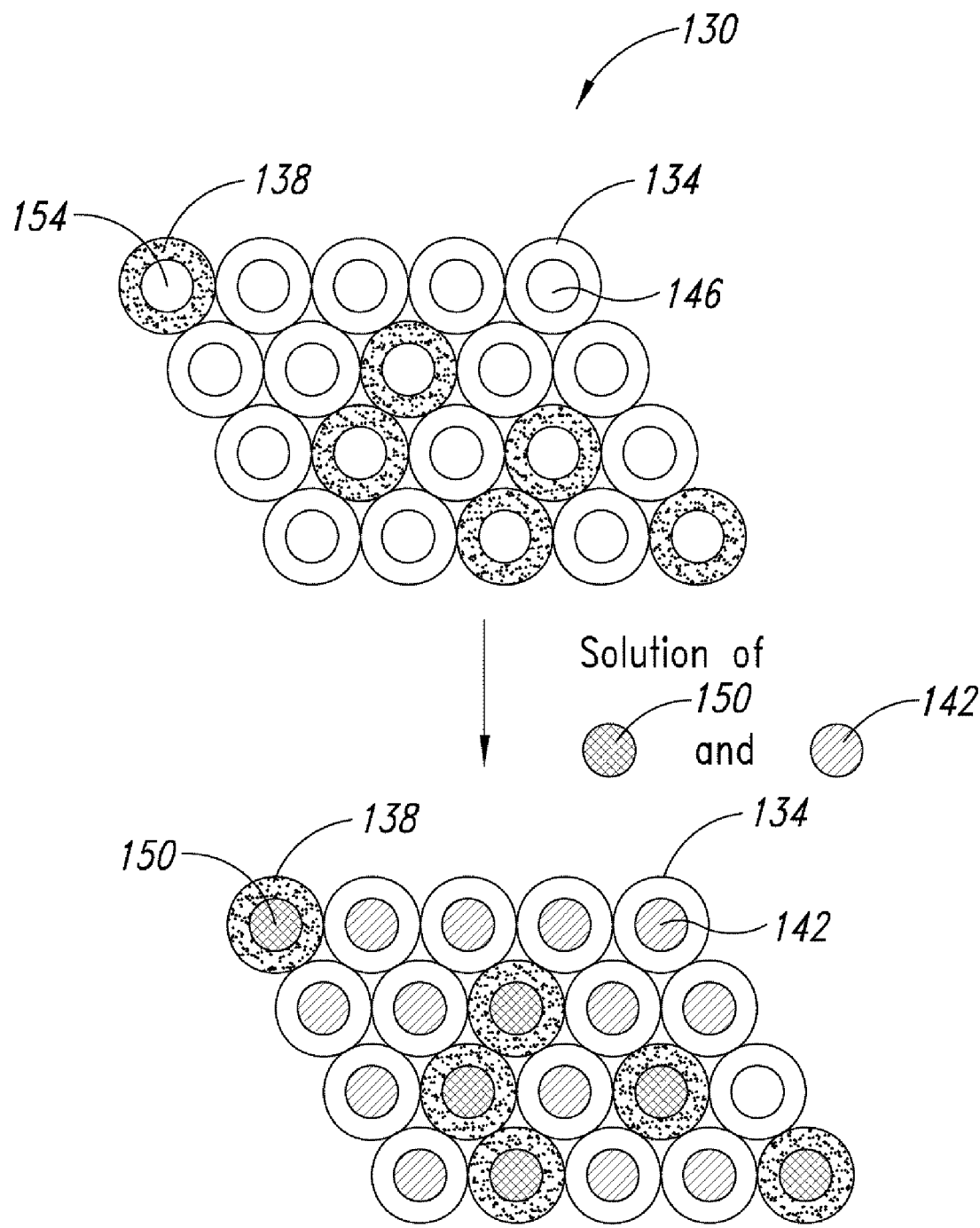
FIG. 6 shows schematically an ordered 2D array of templates according to one embodiment.

FIGS. 5A and 5B show schematically a ring-shaped chaperonin 100 having nine subunits 104. An open pore 108 is positioned in the center of the chaperonin. The open pore can be characterized as a functional domain, which comprises peptide sequences that can be genetically engineered to have specific affinity for nanocrystals of specific materials. In addition, the functional domain has a well-defined geometry that can determine the size of the nanocrystals nucleated thereon.

Through genetic engineering, binding sites (not shown) may be present on each or any number of the subunits. As one example, FIG. 5A shows that four subunits have first binding sites that coupled to a first type of nanocrystals 112, and five subunits having second binding sites that coupled to a second type of nanocrystals 116.

The subunits of the chaperonins can also be engineered to present first binding sites in the open pore and second binding sites on the exterior of the chaperonin. As illustrated in FIG. 5B, chaperonin 102 is bound to nine first nanocrystals 112 in the open pore 108, and to nine nanocrystals 114 of a second type on the exterior 124.

Native chaperonins are subcellular structures composed of 14, 16 or 18 identical subunits called heat shock proteins. These 60 kDa subunits are arranged as two stacked rings 16-18 nm tall by 15-17 nm wide. Many varieties of chaperonins have been sequenced and their structural information is available to guide genetic manipulations. Mutant chaperonins, in which one or more amino acids have been altered through site-directed mutagenesis, can be developed to manipulate the final shape and binding capability of the chaperoning. See, e.g., McMillan A. et al., (2002) *Nature Materials,* 1, 247-252. It should be understood that genetically engineered or chemically modified variants of chaperonins are also suitable templates as defined herein.

In another embodiment, the template is an S-layer protein, which self-assembles into ordered two-dimensional arrays and can bind to nanocrystals. (See, e.g., Pum D. et al., *Nanotechnology* (2000) 11, 100-107.) Native S-layers proteins form the outermost cell envelope component of a broad spectrum of bacteria and archaea. They are composed of a single protein or glycoprotein species (Mw 40-200 kDa) have unit cell dimensions in the range of 3 to 30 nm. S-layers are generally 5 to 10 nm thick and show pores of identical size (e.g., 2-8 nm). It has been demonstrated that S-layer proteins recrystallized on solid surfaces or S-layer self-assembly products deposited on such supports may be used to induce the formation of CdS particles or gold nanoparticles, see, e.g., Shenton et al., *Nature* (1997) 389, 585-587; and Dieluweit et al. *Supramolec Sci.* (1998) 5, 15-19. It should be understood that genetically engineered or chemically modified variants of S-layer protein are also suitable templates as described herein.

In yet another embodiment, the biological template is an apoferritin. Apoferritin is a ferritin devoid of ferrihydrite. Native ferritin is utilized in iron metabolism throughout living species. It consists of 24 subunits, which create a hollow structure having a cavity of roughly 8 nm in diameter surrounded by a wall of about 2 nm in thickness. The cavity normally stores 4500 iron(III) atoms in the form of paramagnetic ferrihydrite. In apoferritin, this ferrihydrite is removed and other nanoparticles may be incorporated in the cavity created. The subunits in a ferritin pack tightly; however, there are channels into the cavity. Some of the channels comprise suitable binding sites that bind metals such as cadmium, zinc, and calcium. Ferritin molecules can be induced to assemble into an ordered arrangement in the presence of these divalent ions. Detailed description of using ferritin as a template for binding to nanocrystals can be found in, e.g., U.S. Pat. Nos. 6,815,063 and 6,713,173. It should be understood that genetically engineered or chemically modified variants of apoferritin are also suitable templates as described herein.

In a further embodiment, the template is an *E. coli* DNA polymerase III β subunit, which is a homo dimeric protein. The overall structure assumes a donut shape with a cavity of about 3.5 nm and a wall of about 3.4 nm thick. The interior surface of the wall comprises twelve short α helices while six β sheets form the outer surface. The interior surface can be engineered to introduce amino acid or peptide sequence that will capture or nucleate nanocrystals of various materials. It should be understood that genetically engineered or chemically modified variants of *E. coli* DNA polymerase are also suitable templates as described herein.

b. Biological Scaffolds

In other embodiments, the template is a biological scaffold to which one or more peptide sequences are fused. "Biological scaffold" refers to a complex multi-molecular biological structure that comprises multiple binding sites. In preferred embodiments, the biological scaffolds are genetically engineered to control the number, distribution, and spacing of the binding sites (e.g., peptide sequences) fused thereto.

Examples of the biological scaffolds include, without limitation, viral particles, bacteriophages, amyloid fibers, and capsids. These biological scaffolds (in both their native and mutant forms) are capable of forming ordered structures when deposited on a variety of solid surfaces. See, e.g., Flynn, C. E. et al., "Viruses as Vehicles for Growth, Organization Assembly of Materials," *Acta Materialia* (2003) 51, 5867-5880; Scheibel, T. et al., *PNAS* (2003), 100, 4527-4532; Hartgerink, J. D. et al., *PNAS* (2002) 99, 5133-5138; McMillan, A. R. et al., *Nature materials* (2002), 247-252; Douglas, T. et al., *Advanced Materials* (1999) 11, 679-681; and Douglas, T. et al., *Adv. Mater.* (2002) 14, 415-418; and Nam et al., "Genetically Driven Assembly of Nanorings Based on the M3 Virus," *Nanoletters,* a-e.

In one particular embodiment, a M13 bacteriophage can be engineered to have one or more particular peptide sequences fused onto the coat proteins. For example, it has been demonstrated that peptide sequences with binding and/or nucleating affinity for gold or silver nanocrystals can be introduced into the coat protein (see, e.g., U.S. patent application Ser. No. 11/254,540.)

In another embodiment, amyloid fibers can be used as the biological scaffold on which nanoparticles can bind and assemble into an ordered nanoscale structure. "Amyloid fibers" refer to proteinaceous filament of about 1-25 nm diameters. Under certain conditions, one or more normally soluble proteins (i.e., a precursor protein) may fold and assemble into a filamentous structure and become insoluble. Amyloid fibers are typically composed of aggregated β-strands, regardless of the structure origin of the precursor protein. As used herein, the precursor protein may contain natural or unnatural amino acids. The amino acid may be further modified with a fatty acid tail. Suitable precursor proteins that can convert or assemble into amyloid fibers include, for example, RADA16 (Ac-R+AD-AR+AD-AR+AD-AR+AD-A-Am) (gold-binding) (SEQ ID NO:1), biotin-R(+)GD(−)SKGGGAAAK-NH$_2$ (gold-binding) (SEQ ID NO:2), WSWR(+)SPTPHVVTD(−)KGGGAAAK-NH$_2$ (silver-binding) (SEQ ID NO:3), AVSGSSPD(−)SK(+)KGG- GAAAK-NH$_2$ (gold-binding) (SEQ ID NO:4), and the like. See, e.g., Stupp, S. I. et al., *PNAS* 99 (8) 5133-5138, 2002, and Zhang S. et al., PNAS 102 (24) 8414-8419, 2005.

Similar to protein templates, biological scaffolds are also preferred to be engineerable such that peptide sequences can be selectively expressed and distributed according to a certain ratio.

c. Assembling and Aggregation of the Biological Templates

The alloy formation relies on the assembling or aggregation of the templates, which brings the nanocrystals bound to each template into close proximity. In certain embodiments, the templates can assemble prior to binding to the nanocrystals. In other embodiments, the templates can be bound with nanocrystals prior to assembling.

Biological templates such as biomolecules and biological scaffolds have a natural tendency to aggregate in solutions or on a substrate. Some biological templates can spontaneously self-assemble into highly crystalline 2D or 3D structures.

FIG. 6 shows schematically an ordered 2D array 130 of templates formed by the aggregation of two types of chaperonins 134 and 138. The first type of chaperonins 134 is capable of binding to first nanocrystals 142 within its open pore 146. The second type of chaperonins 138 is capable of binding to second nanocrystals 150 within its open pore 154. In this embodiment, the 2D array 130 comprises 30% the first type of chaperonins 134 and 70% of the second type of chaperonins 138, which correspond to 30% of the first nanocrystals 142 and 70% of the second nanocrystals 150. As illustrated, the relative components of the first and second nanocrystals in a resulting alloy are determined by the ratio of their corresponding templates.

It is noted that the templates can also be deposited or assembled to form random, polycrystalline or amorphous structures, so long as the templates selected comprise the desired ratio of the first and second binding sites, whether they are present on the same type of template or present on corresponding first and second type of templates.

2. Nonbiological Templates

The template may also be an inorganic template, for example, silicon, germanium, quartz, sapphire, or any other acceptable material. This template can be coupled to an appropriate ratio of binding sites that have specific affinities for the desired components. For example, binding sites (e.g., proteins such as streptavidin or avidin) can be immobilized at selected locations and at selected ratios to an inorganic template, e.g., silicon. Nanocrystals or other nanoparticles can be directly coupled to the binding sites. Alternatively, the nanocrystals can be initially coupled to a binding partner of the binding sites (e.g. a biotin for streptavidin) thereby become immobilized on the silicon substrate through the strong affinity between the binding partners (e.g. biotin and streptavidin).

It should be understood that other binding sites, such as self-assembled single layers comprising functional groups, can be used to immobilize and template nanocrystals that have a specific affinity for the functional group.

It is important that the binding sites (e.g., streptavidin) be patterned on the inorganic template within nanometers to tens of nanometers from each other to ensure that the nanocrystals bound thereto are also appropriately spaced. Protein immobilization and patterning on a substrate can be achieved by any known methods in the art. For example, streptavidin can be patterned on a silicon oxide substrate in nanoscale resolutions by nanoimprint lithography, see, e.g., Hoff, J. D. et al., *Nano Letters* (4) 853, 2004.

B. Binding Sites

As discussed above, the templated formation of a digital alloy is ultimately controlled by the nature, spacing and the relative ratio of at least two types of binding sites on a template. "Binding site," or "binding sequence," refers to the minimal structural elements within the template that are associated with or contribute to the template's binding activities. Preferably, the binding sites can control the composition, size and phase of the nanocrystals that will be coupled thereto.

As used herein, the terms "bind" and "couple" and their respective nominal forms are used interchangeably to generally refer to a nanocrystal being attracted to the binding site to form a stable complex. The underlying force of the attraction, also referred herein as "affinity" or "binding affinity," can be any stabilizing interaction between the two entities, including adsorption and adhesion. Typically, the interaction is non-covalent in nature; however, covalent bonding is also possible.

Typically, a binding site comprises a functional group of the biomolecule, such as thiol (—SH), hydroxy (—OH), amino (—NH$_2$) and carboxylic acid (—COOH). For example, the thiol group of a cysteine effectively binds to a gold particle (Au). More typically, a binding site is a sequence of subunits of the biomolecule and more than one functional groups may be responsible for the affinity. Additionally, conformation, secondary structure of the sequence and localized charge distribution can also contribute to the underlying force of the affinity.

"Specifically binding" and "selectively binding" are terms of art that would be readily understood by a skilled artisan to mean, when referring to the binding capacity of a biological template, a binding reaction that is determinative of the presence of nanocrystals of one material in a heterogeneous population of nanocrystals of other materials, whereas the other materials are not bound in a statistically significant manner under the same conditions. Specificity can be determined using appropriate positive and negative controls and by routinely optimizing conditions.

The composition of peptide sequences on a template is fixed to create a selected composition of nanoparticle building blocks, and various different peptide sequences can be arranged on the templates in a random or an ordered way. The composition of a mixture of templates, each designed with at least one peptide sequence with selective affinity of the material of one of the nanoparticle building blocks, can be chosen to yield a given composition of nanoparticle building blocks. The templates themselves may be deposited or may self-assemble in a random or an ordered way.

An evolutionary screening process can be used to select the peptide sequence that has specific binding affinities or selective recognition for a particular material. Detailed description of this technique can be found in, e.g., U.S. Published Patent Application Nos. 2003/0068900, 2003/0073104, 2003/0113714, 2003/0148380, and 2004/0127640, all of which in the name of Cambrios Technologies Corporation, the assignee of the present application. These references, including the sequence listings described, are incorporated herein by reference in their entireties.

In brief, the technique makes use of phage display, yeast display, cell surface display or others, which are capable of expressing wide variety of proteins or peptide sequences. For example, in the case of phage display, libraries of phages (e.g., M13 phages) can be created by inserting numerous different sequences of peptides into a population of the phage. In particular, the genetic sequences of the phage can be manipulated to provide a number of copies of particular peptide sequences on the phage. For example, about 3000 copies of pVIII proteins can be arranged in an ordered array along the length of M13 phage particles. The pVIII proteins can be modified to include a specific peptide sequence that can nucleate the formation of a specific target nanocrystal. The proteins having high affinities for different, specific target nanocrystal can be exposed to more and more stringent environment till one can be selected that has the highest affinity. This protein can then be isolated and its peptide sequence identified.

This technique is powerful because it allows for rapid identification of peptide sequence that can bind, with specificity, to nanocrystals of any given material. Moreover, as will be discussed in more detail below, once a peptide sequence is identified, it can be incorporated into a biological template in a controllable manner through genetic engineering.

The binding site can be coupled to an appropriate nanocrystal through direct binding or "affinity." In this case, preformed nanocrystals of pre-determined compositions and dimensions can be incubated together with the templates and binding reactions take place between appropriate binding sites and the nanocrystals.

It is also possible that the templates can cause the nanocrystals to nucleate from a solution phase on to the template. Nucleation is a process of forming a nanocrystal in situ by converting a precursor in the presence of a template. Typically, the in situ generated nanocrystals bind to the template and continue to grow. As noted above, certain biological templates (e.g., proteins such as chaperonins and apoferritins) have a functional domain of controllable composition and geometry. The functional domain therefore provides both the binding site as well as the physical constraints such that the nucleated nanocrystals can grow into a controllable dimension (determined by the geometry of the functional domain). Detailed description of forming nanoparticles by nucleation process can be found in, e.g., Flynn, C. E. et al., (2003) *J. Mater. Sci.*, 13, 2414-2421; Lee, S-W et al., (2002) *Science* 296, 892-895; Mao, C. B. et al., (2003) *PNAS*, 100, (12), 6946-6951, and U.S. Published Patent Application No. 2005/0164515.

Table 1 shows examples of peptide sequences that have been identified to have specific affinity to a number of semiconductor and metallic materials. The mechanisms with which the peptide sequence interacts with a given material are also indicated.

TABLE 1

| Peptide Sequence | Material | Type of Binding |
|---|---|---|
| CNNPMHQNC (SEQ ID NO: 5) | ZnS | nucleation, affinity[1,2,3,4] |
| LRRSSEAHNSIV (SEQ ID NO: 6) | ZnS | nucleation, affinity[1,3,4] |
| CTYSRLHLC (SEQ ID NO: 7) | CdS | nucleation, affinity[1] |
| SLTPLTTSHLRS (SEQ ID NO: 8) | CdS | nucleation, affinity[1] |
| HNKHLPSTQPLA (SEQ ID NO: 9) | FePt | nucleation, affinity[6,7] |
| CNAGDHANC (SEQ ID NO: 10) | CoPt | nucleation, affinity[6] |
| SVSVGMKPSPRP (SEQ ID NO: 11) | L10 FePt: | nucleation, affinity[7] |

TABLE 1-continued

| Peptide Sequence | Material | Type of Binding |
|---|---|---|
| VISNHRESSRPL (SEQ ID NO: 12) | L10 FePt: | nucleation, affinity[7] |
| KSLSRHDHIHHH (SEQ ID NO: 13) | L10 FePt: | nucleation, affinity[7] |
| VSGSSPDS (SEQ ID NO: 14) | Au | nucleation, affinity[8] |
| AEEEED (SEQ ID NO: 15) | Ag, $Co_3O_4$ | nucleation, affinity[9] |
| KTHEIHSPLLHK (SEQ ID NO: 16) | CoPt | Affinity |
| EPGHDAVP (SEQ ID NO: 17) | $Co^{2+}$ | nucleation, affinity[11] |
| HTHTNNDSPNQA (SEQ ID NO: 18) | GaAs | affinity[12,13] |
| DVHHHGRHGAEHADI (SEQ ID NO: 19) | CdS | nucleation, affinity[14] |
| KHKHWHW (SEQ ID NO: 20) | ZnS, Au, CdS | affinity[15] |
| RMRMKMK (SEQ ID NO: 21) | Au | affinity[15] |
| PHPHTHT (SEQ ID NO: 22) | ZnS | affinity[15] |
| CSYHRMATC (SEQ ID NO: 23) | Ge dislocations | affinity[16] |
| CTSPHTRAC (SEQ ID NO: 24) | Ge dislocations | affinity[16] |
| LKAHLPPSRLPS (SEQ ID NO: 25) | Au | affinity[9] |

[1]Flynn, C. E. et al., "Synthesis and organization of nanoscale II-VI semiconductor materials using evolved peptide specificity and viral capsid assembly," (2003) J. Mater. Sci., 13, 2414-2421.
[2]Lee, S-W et al., "Ordering of Quantum Dots Using Genetically Engineered Viruses," (2002) Science 296, 892-895.
[3]Mao, C. B. et al., "Viral Assembly of Oriented Quantum Dot Nanowires," (2003) PNAS, vol. 100, no. 12, 6946-6951.
[4]US2005/0164515
[6]Mao, C. B. et al., "Virus-Based Toolkit for the Directed Synthesis of Magnetic and Semiconducting Nanowires," (2004) Science, 303, 213-217.
[7]Reiss, B. D. et al., "Biological route to metal alloy ferromagnetic nanostructures" (2004) Nano Letters 4(6), 1127-1132.
[8]Huang, Y. et al., "Programmable assembly of nanoarchitectures using genetically engineered viruses" (2005) Nano Letters 5(7), 1429-1434.
[9]U.S. patent application Ser. No. 11/254,540.
[11]Lee, S-W. et al., "Cobalt ion mediated self-assembly of genetically engineered bacteriophage for biomimic Co-Pt hybrid material" Biomacromolecules (2006) 7(1), 14-17.
[12]Whaley, S. R. et al., "Selection of peptides with semiconductor binding specificity for directed nanocrystal assembly" (2000) Nature, 405(6787), 665-668.
[13]US2003/0148380
[14]US2006/0003387
[15]Peelle, B. R. et al., "Design criteria for engineering inorganic material-specific peptides" (2005) Langmuir 21(15), 6929-6933.
[16]U.S. Provisional Patent Application No. 60/620,386.

C. Nanocrystals

"Nanocrystal", "quantum dots", or "nanoparticles" generally refers to a nanoscale building block of the digital alloy. Nanocrystals are aggregates or clusters of a number of atoms, typically of an inorganic material. As used herein, nanocrystals are typically less than 10 nm in diameter. More typically, the nanocrystals are less than 5 nm in diameter or less than 1 nm in diameter. They may be crystalline, polycrystalline or amorphous.

As described above, nanocrystals of at least two different compositions (materials) are bound to a template or place in an aggregation to form an alloy composition. In certain embodiments, a nanocrystal can be an elemental material, including metals and semiconductors. In other embodiments, a nanocrystal can be a binary material, which is a stable compound or alloy of two elements.

The composition of a nanocrystal thus can be represented by formula $A_mB_n$, wherein A and B are single elements. The letters m and n denote the respective atomic percentages of A and B in the nanocrystal, and are defined as $0 \leq m \leq 1$; $0 \leq n \leq 1$; $m+n=1$; provided that m and n are not 0 at the same time. When n is 0, the nanocrystal is an elemental material A. When neither m nor n is 0, the nanocrystal is a binary compound $A_mB_n$.

Similarly, nanocrystals of a different or second material can be represented by formula $C_pD_q$, in which C and D are single elements and p and q have values $0 \leq p \leq 1$; $0 \leq q \leq 1$; $p+q=1$; provided that p and q are not 0 at the same time.

As used herein, m and n (or p and q) are the respective atomic percentages (atomic %) and correspond to the stoichiometric ratio of A and B in the binary compound. They can also be in the form of proper fractions. For example, a binary compound having 50% A and 50% B can be represented by $A_{0.5}B_{0.5}$. It should be understood that, although m and n are defined as proper fractions or atomic percentages, both of which require that $0 \leq m \leq 1$ and $0 \leq n \leq 1$, the binary compound of $A_mB_n$ can also be expressed in formulae containing whole numbers. One skilled in the art readily recognizes that these formulae are merely different expressions of the same composition. For example, $A_{0.5}B_{0.5}$ may be expressed as $AB$, $A_2B_2$ or $A_5B_5$, or any number of expressions so long as the stoichiometric ratio of A and B (m:n) remains the same. These expressions should therefore be recognized as equivalent compositions of $A_mB_n$.

1. Elemental Material (n=0)

Suitable metallic elements include, Ag, Au, Sn, Zn, Ru, Pt, Pd, Cu, Co, Ni, Fe, Cr, W, Mo, Ba, Sr, Ti, Bi, Ta, Zr, Mn, Pb, La, Li, Na, K, Rb, Cs, Fr, Be, Mg, Ca, Nb, Tl, Hg, Rh, Sc, Y. Suitable semiconductor elements include Si and Ge.

In certain embodiments, nanocrystals of an elemental material can be alloyed with a different elemental material to form a binary alloy. In other embodiments, nanocrystals of an elemental material can be alloyed with a binary compound to form a ternary alloy.

2. Binary Material ($m \neq 0$ and $n \neq 0$)

A binary material is a stable compound of two elements. In certain embodiments, the binary material or binary compound is metallic, including two metallic elements, such as Cu and Ni, Sn and In and the like.

In other embodiments, the binary material is a semiconductor compound. Typically, when A is a Group IIIA element (e.g., Al, Ga, In or Tl), B is a Group VA element (e.g., N, P, As or Sb). When A is a Group IIB element (e.g., Zn, Cd or Hg), B is a Group VIA element (O, S or Se). Many binary semiconductors with stable compositions are known, including, without limitation, AlAs, AlP, AlN, GaAs, GaP, GaN, InAs, ZnSe, CdS, InP and InN and the like.

In certain embodiments, a first binary material ($A_mB_n$) and a second binary material $C_pD_q$ are combined on a template to form a quaternary alloy, in which all four elements A, B, C and D are different elements. In other embodiments, B and D are the same element, and the second binary material can be represented by $C_pB_q$. The resulting composition is therefore a ternary alloy comprising A, B and C.

Metallic and semiconductor nanocrystals are commercially available from, e.g., Quantumsphere, Inc. (Santa Ana, Calif.), Invitrogen (Carlsbad, Calif.), and Nanoprobes (Yaphank, N.Y.). They can also be prepared by known methods in the art, e.g., by sol-gel technique, pyrolysis of organometallic precursors, and the like. These preformed nanocrystals are prepared independently of the templates, and can be coupled to the appropriate binding sites of the template through specific affinity. For example, a pre-formed nanoparticle can bind directly to a binding site, typically a peptide sequence screened and identified for that particular nanoparticle. Alternatively, the nanoparticles can be surface-modified with a desired binding agent, such as biotin, which can be coupled to a binding site (e.g., streptavidin) through the strong and specific affinity between biotin and streptavidin.

In other embodiments, the nanocrystals can be nucleated from a solution phase. Nucleation is a process of forming a nanocrystal in situ by converting a precursor in the presence of a template. Typically, the in situ generated nanoparticle binds to and grows at least partially within the functional domain of the template. The precursors are typically soluble salts of the elements that ultimately form the nanocrystals. For example, nanocrystals of CdS can be nucleated out of a solution containing $Cd^{2+}$ and $S^{2-}$. More detailed description of forming nanoparticles by nucleation process can be found in, e.g., Flynn, C. E. et al., "Synthesis and Organization of Nanoscale II-VI Semiconductor Materials Using Evolved Peptide Specificity and Viral Capsid Assembly," (2003) *J. Mater. Sci.*, 13, 2414-2421; Lee, S-W et al., "Ordering of Quantum Dots Using Genetically Engineered Viruses," (2002) *Science* 296, 892-895; Mao, C. B. et al., "Viral Assembly of Oriented Quantum Dot Nanowires," (2003) *PNAS*, vol. 100, no. 12, 6946-6951, and US2005/0164515.

D. Alloys

As discussed above, by controlling the relative amount (x:y) of the first binding sites and the second binding sites on a template, the first nanocrystals of the first material and the second nanocrystals of the second material can be modulated to form an alloy. In particular, where the first material is a compound represented by $A_mB_n$, and the second material is a compound represented by $C_pD_q$, the resulting alloy can be represented by $(A_mB_n)_x(C_pD_q)_y$, wherein, $0 \leq m \leq 1$; $0 \leq n \leq 1$; $m+n=1$; and $0 \leq p \leq 1$; $0 \leq q \leq 1$; and $p+q=1$, provided that m and n are not 0 at the same time, and p and q are not 0 at the same time.

In certain embodiments, A, B, C and D are different from one another and the resulting alloy is a quaternary alloy.

In other embodiments, A, B and C are different from one another, and B is the same as D, and the resulting alloy is a ternary alloy.

In yet other embodiments, $n=q=0$, and the resulting alloy is a binary alloy $A_xC_y$, or $A_xC_{1-x}$ (as $x+y=1$).

Alloys with versatile compositions can be achieved by selecting the appropriate nanocrystal components and by controlling the relative amount of the corresponding binding sites on the templates.

For example, InN and GaN can be selected as the nanocrystal components to form an alloy of $(InN)_x(GaN)_y$, or $In_xGa_yN_{x+y}$, in the presence of templates that provide, in percentages, x binding sites that bind specifically with InN and y binding sites that bind specifically with GaN. Because $x+y=1$, the resulting alloy can also be represented by $In_xGa_{1-x}N$. Thus, alloys having a variety of bandgaps can be obtained by controlling the amounts of the respective binding sites. The formations of these alloys are not restrained by lattice matching. More specifically, because the alloys are built from nanoscale building blocks (nanostructure components) on molecular level, strains and defects typically associated with epitaxial growth are not of concern.

Other alloys that correspond to useful bandgaps include, for example, $GaAs_xP_{1-x}$ (formed from GaP and GaAs), $Ga_xIn_{1-x}P$ (formed from GaP and InP), $Al_xIn_{1-x}P$ (formed from AlP and InP) and $Al_xGa_{1-x}As_yP_{1-y}$ (formed from AlP and GaAs).

E. Method of Making Digital Alloys

Other embodiments describe a method of making an alloy comprising:

selecting biological templates having, in percentages, x first binding sites and y second binding sites (0<x<1, 0<y<1), the first binding site having a specific binding affinity for a first nanoparticle of a first material, the second binding site having a specific binding affinity for a second nanoparticle of a second material;

binding the first nanoparticles to respective first binding sites, binding the second nanoparticles to respective second binding sites; and forming the alloy comprising the first material and the second material at a stoichiometric ratio of x:y.

In certain embodiments, the first material is a compound represented by $A_mB_n$, the second material is a compound represented by $C_pD_q$, the resulting alloy can be represented by $(A_mB_n)_x(C_pD_q)_y$, wherein, $0 \leq m \leq 1$; $0 \leq n \leq 1$; m+n=1; and $0 \leq p \leq 1$; $0 \leq q \leq 1$; and p+q=1, provided that m and n are not 0 at the same time, and p and q are not 0 at the same time.

In other embodiments, selecting the biological templates comprises engineering the biological templates through genetic manipulation. In particular, controlling the biological template can be accomplished by engineering the biological template to express the first binding sites (e.g., first peptide sequence) and the second binding sites (e.g., second peptide sequence) at pre-determined locations, spacings and quantities on the templates.

In a preferred embodiment, the biological template is a protein. Exemplary proteins include, without limitation, a chaperonin or a genetically engineered or chemically modified variant thereof, a S-layer protein or a genetically engineered or chemically modified variant thereof, an apoferritin or a genetically engineered or chemically modified variant thereof, or an *E. coli* DNA polymerase III β subunit or a genetically engineered or chemically modified variant thereof.

In other embodiments, the biological template is a biological scaffold fused with the first peptide sequence and the second peptide sequence. As discussed above, a biological scaffold can be, for example, a viral particle, a bacteriophage, an amyloid fiber, or a capsid.

FIG. 7 illustrates a method of making a digital alloy, starting with a template 151 which has been engineered to have the desired ratio of binding sites that cause the formation of a material which emulates a ternary compound of $Al_xGa_{1-x}As$. The template 151 has a first plurality of binding sites 152 which have an affinity for nanocrystal 156, in this example AlAs. The template also contains a second plurality of binding sites 154 which have an affinity for nanocrystal 158, in this embodiment GaAs. The ratio of the first binding sites 152 to the second binding sites 154 is selected to achieve a desired composition of the resulting alloy. For example, an M13 virus can be genetically modified to have binding sites (e.g., peptide sequences) for these or other selected nanocrystals at particular locations on the outer coat proteins of the virus. The template 151 is then exposed to a fluid having a plurality of nanoparticles of the binary compound AlAs.

The AlAs nanoparticles can selectively affix themselves to the respective binding sites 152 of the template 151 and do not affix or attach to the binding sites 154. The template 151 is also exposed to a fluid having GaAs nanoparticles therein and the GaAs nanoparticles affix themselves to the binding sites 154. In some embodiments, it is desired to have the fluids in separate liquid solutions and the template is sequentially exposed to the fluids, while in other embodiments, the template may be exposed simultaneously to a single liquid solution having both binary components therein.

FIGS. 8 and 9 illustrate the various steps for forming a ternary compound material according to one embodiment. In the step shown in FIG. 8, any acceptable substrate, such as a template 168 is provided as previously illustrated and explained with respect to FIG. 7. The template 168 has a plurality of binding sites 164 and 167 thereon, having respective affinities for the desired nanocrystal component. The nanocrystal components which are to form the digital alloy can have any desired element composition. In the example provided for FIGS. 8-11, they are binary compositions such as InN and GaN. It is desired that the binding sites be close enough to form a continuous material from an electron's point of view. The spacings between adjacent binding sites are typically on the order of nanometers and tens of nanometers. The ratio of the binding sites 164 and 167 is selected to provide the desired number of the components of binary component 160 and binary component 162. Accordingly, template 168 is engineered to contain different binding sites that can selectively attach to the respective nanocrystals. In addition, the binding sites are spaced several nanometers (e.g., less than 10 nm) apart from each other in order to provide a continuous material A solution is provided having a plurality of the nanocrystals 160 and 162 evenly dispersed therethrough. The nanocrystals may be in the form of nanoparticles, nanorods, or any other acceptable form. In one embodiment, a single solution is provided which has both types of nanocrystals present. Alternatively, two separate solutions can be provided, each of which have the nanocrystals present, evenly dispersed. A plurality of templates 168 is placed into the solution containing the nanocrystals. The solution can be mixed at room temperature and contains the appropriate pH balances such that the template 168 is active using techniques well known in the art. A plurality of the templates 159 can be deposited or self-assemble on a substrate to provide a layer of the alloy, the controllable composition of which corresponds to desired physical properties.

If the nanocrystals are in two separate solutions, the template 168 is placed in a first solution and mixed until the binding sites for that particular nanocrystal have become attached to the appropriate nanoparticles in solution, and then the template 168 is removed from the first solution and placed in the second solution which contains the second nanocrystals 160, and the mixing continued.

When such a template is exposed to a solution having nanoparticles or quantum dots composed of material which have an affinity to the respective binding sites, then the materials will bind to the templates, which can form an ordered array of the material so that the final templates 168 emulate a ternary alloy having three different elements in respective ratios rather than two different binary compounds. The use of nanocrystals, quantum dots, and nanoparticles permit the templated formation of such nanoscale materials which will emulate for physical, chemical, and electric purposes a ternary alloy.

The template 168 can be constructed to build many different alloys of different compositions. For example, the pVIII protein can be engineered with particular peptide sequences for use as a template. The peptide sequences to provide selective affinity and linking to various semiconductor nanocrystals, such as ZnS or CdS, are known or can be screened and identified by known methods. For example, an A7 and a Z8 peptide on a pVIII protein are known to recognize and control the growth of ZnS while a J140 provides selective recognition of CdS. See "Viral assembly of oriented quantum dot nanowires" by Mao et al. *PNAS*, Jun. 10, 2003, Vol. 100, No. 12 and "Synthesis and organization of nanoscale II-VI semiconductor materials using evolved peptide specificity and viral capsid assembly" by Flynn et al. *J. Mater. Chem.*, 2003, Vol. 13, pages 2414-2421, each of which is incorporated herein by reference.

Other templates using different peptide combinations can be used to create substrates for forming compositions having In, Ga, Al, As, N, P, and various other elements in binary compositions to emulate a ternary or quaternary compound.

One strength of the technique is that the very same binary components can be used to create different ternary compounds having different bandgaps using the same nanoparticles, as illustrated in FIGS. 10 and 11. As illustrated in FIG. 10, a template 161 is provided having a first selected ratio of binding sites 167 to binding sites 164. In the example shown, there are eight binding sites 167 for every two binding sites 164. When the template 161 is exposed to a liquid solution having a plurality of nanoparticles of InN 160 and GaN 162, the respective nanoparticles bind to the binding sites for which they have a specific affinity, thus creating a final composition of $In_{0.2}Ga_{0.8}N$.

FIG. 11 illustrates a different template 163 in which the same binding sites 164 and 167 are engineered to have a different ratio with respect to each other. In this example, the binding sites 164 have a ratio to the binding sites 167 of 3:7 or 30%:70%. Accordingly, when the template 163 is exposed to the same liquid solution having the binary nanoparticles, a different ratio of the nanocrystals affixes to the template. In the event the nanoparticles are InN and GaN, a final composition will be formed having the properties of $In_{0.3}Ga_{0.7}N$. Any desired ratio of the nanocrystal components can be formed in the presence of templates, which in turn controls the final alloy composition, such as $In_{0.35}Ga_{0.65}N$, etc.

F. Applications

Alloys compositions described herein correspond to useful opto-, electrical and mechanical properties that may not be attainable through conventional means of multi-component alloying or compounding. Driven by the powerful techniques of genetically engineering a given biological template, alloys of highly customizable compositions can be obtained by controlling the different binding sites on the templates that correspond to respective nanocrystals components.

Thus, various embodiments are directed to devices that utilize alloy compositions described herein.

1. Photovoltaic Cells or Solar Cells

Solar radiation provides a usable energy in the photon range of approximately 0.4 eV to 4 eV. Optoelectronic devices such as photovoltaic cells can harvest and convert certain photon energies in this range to electrical power. Typically, the optoelectrical device is based on a semiconductor material with a direct bandgap that matches a given photon energy. With the absorption of the photon energy, electrons in the valence band can be excited to the conduction band, where the electrons are free to migrate. Similarly, holes are generated in the valence band. The migration of these charge carriers (e.g., electrons and holes) forms an electrical current.

The bandgaps of currently available semiconductor materials only correspond to a narrow portion within the broad range of the solar radiation. Light with energy below the bandgap of the semiconductor will not be absorbed or converted to electrical power. Light with energy above the bandgap will be absorbed, but electron-hole pairs that are created quickly recombine and lose the energy above the bandgap in the form of heat. For example, photovoltaic cells based on crystalline silicon have a direct bandgap of about 1.1 eV, lower than most of the photon energies. Silicon-based solar cells therefore have about 25% efficiency at best.

Thus, existing photovoltaic cells have intrinsic efficiency limits imposed by the semiconductor materials. Currently, no one semiconductor material has been found that can completely match the broad ranges of solar radiation.

Higher efficiencies have been sought by using stacks of semiconductors with different bandgaps, which provide solar cells having one or more junctions. Stacks formed from two semiconductors, $Ga_{0.5}In_{0.5}P/GaAs$ and three semiconductors $Ga_{0.5}In_{0.5}P/GaAs/Ge$ have been developed over the last decade. These multi-junction cells take advantages of the relatively good lattice match of $Ga_{0.5}In_{0.5}P$, GaAs and Ge. Typically, in a multi-junction cell with layers of different compositions, lattice matching is critical in producing low-defect or defect-free crystals. Crystal defects negatively impact the optical properties of the semiconductor because the defects trap charge carriers and limit the current and voltage obtainable. Accordingly, multi-junction cells are typically limited by a general lack of appropriate semiconductor materials that can be integrated at low cost.

It was recently realized that the ternary alloys ($In_xGa_{1-x}N$) could be used as the basis of a full-spectrum solar cell, see, U.S. Published Patent Application 2004/0118451, but many technical challenges remain in growing well-controlled, epitaxial layers of $In_xGa_{1-x}N$.

The semiconductor alloys described herein provide tunable bandgaps through compositional control in the presence of templates, without the concerns of lattice and polarity match. It is possible to create alloy compositions with bandgaps that correspond to the entire range of the solar radiation.

Figure 12A:
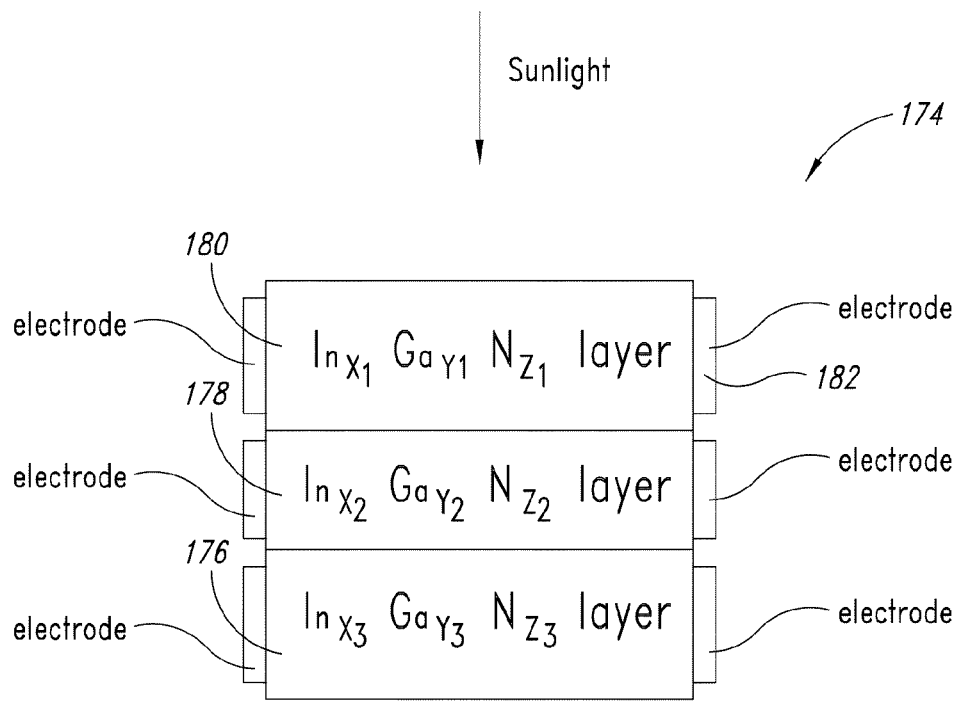
FIGS. 12A and 12B illustrate a solar cell having a plurality of layers which emulate ternary compounds made according to principles illustrated in FIGS. 10 and 11.
Figure 12B:
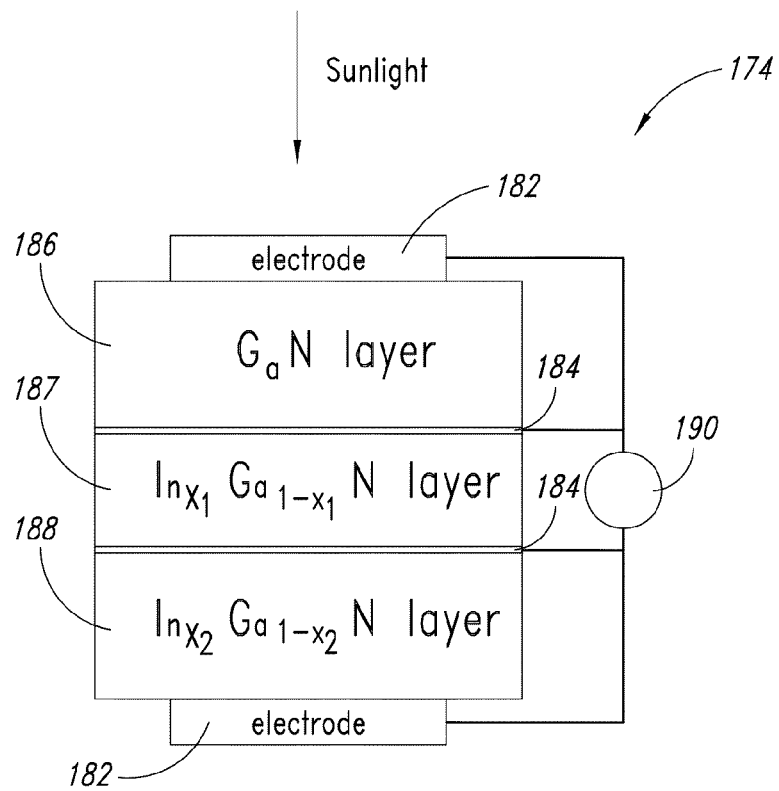

FIGS. 12A and 12B illustrate solar cells 174 composed using an array of digital alloys according to principles of the present invention. The solar cell 174 is composed of a semiconductor material having three layers of a customized digital composition made as described herein. The solar cell 174 has electrodes 182 on a side region thereof. In one embodiment, a low resistance electrical layer composed of a highly doped semiconductor or some other contact material is coupled to an electrode in the top region thereof. It is also known in the art to use a GaAs substrate as a base material to which a conducting electrode is affixed in order to complete the electrical circuit for the generation of electricity from the solar cell, and such structures fall within the use of this invention, even though not shown in the figures. A GaAs layer by itself is known to produce electricity when exposed to sunlight at efficiencies in the range of 16%-25% with efficiencies of 20%-25% being achieved. This efficiency can be substantially improved using structures as disclosed herein.

As shown in FIG. 12A, a solar cell is formed that is composed of a plurality of digital alloys constructed using the methods disclosed herein, as previously illustrated with respect to FIGS. 7-11. A layer or large array of digital alloys templates constructed based on the principals of FIGS. 7-11 are formed into three separate layers 176, 178, and 180. The ratio of the nanocomponents in the layer 176 is selected to emulate a ternary compound having the properties of $In_{x3}Ga_{y3}N$. This material will have the desired bandgap and electrical properties when exposed to sunlight to produce electricity from different frequencies of sunlight than that which are produced by the layers 178 and 180. Accordingly, the layer 176 will be extracting energy from different portions of the light frequency than is being extracted by layers 178 and 180, thus resulting in greater overall efficiencies of the solar cell 174.

Similarly, layers 178 and 180 are formed adjacent to and on top of the layer 176 into a single structure. These layers are also composed of a plurality of binary nanocrystals of the very same binary compounds of InN and GaN, but different ratios. The respective ratios of the compounds are varied in order to emulate a quaternary compound having the optoelectrical properties to extract energy from different parts of the sunlight spectrum. Since the same binary materials are used, it is possible in some structures that the crystalline lattice structure will be compatible and the adjacent layers 178 and 180 can be formed in the same crystalline structure and in physical contact with each other. The three, four, or five layers of semiconductors, each having a slightly different ratio of elements, provides a very efficient solar cell.

Figure 1:
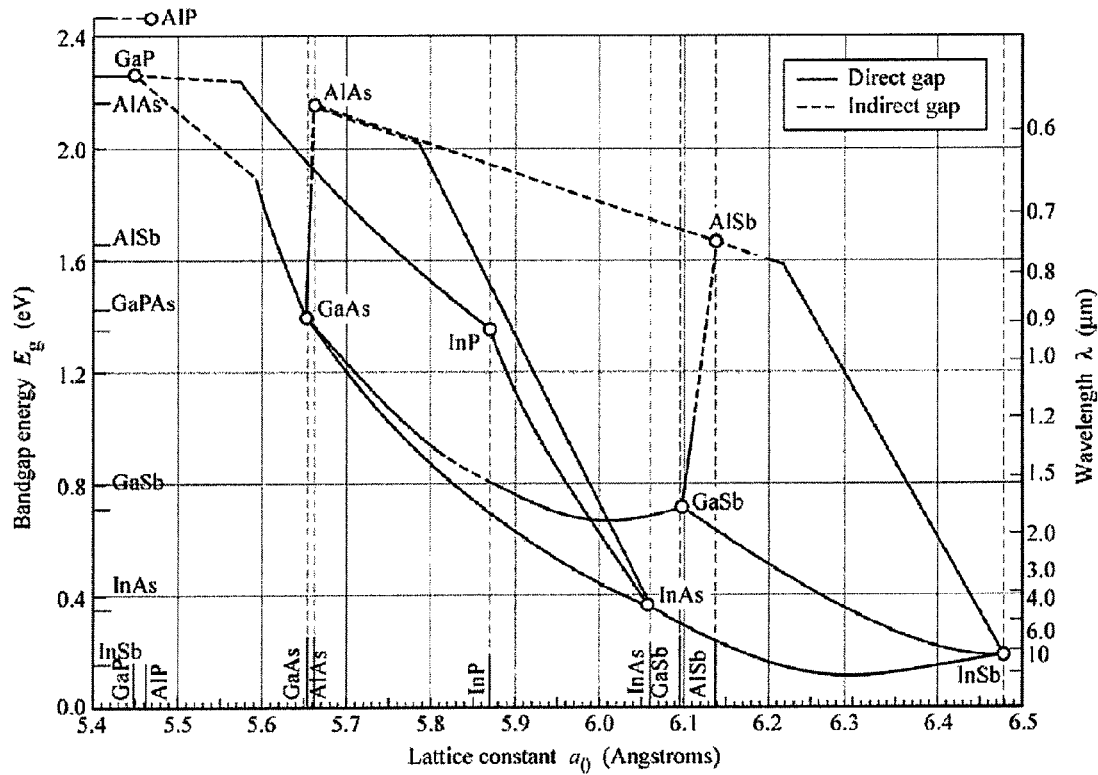
FIG. 1 is a well-known bandgap energy and lattice constant graph.

As shown in FIGS. 12A-12B, a solar cell 174 can, of course, be composed of a wide variety of different digital alloy materials using any combination of the nanocrystals or nanoparticles disclosed in the application. For example, the digital alloys for any one of layers 176, 178, and 180 may include compounds that include additional elements such as P, Al, Cd, cadmium-selenide, cadmium-telluride and other materials. One advantage of the present invention is that the different components need not have similar lattice constants and may not alloy or chemically bind to each other under standard conditions. For example, GaP may be formed in the same digital alloy with InSb or InAs using binding sites adjacent to each other along a template according to principles discussed herein. Since these materials have vastly different lattice constants, forming them in the same substrate in a conventional cell would be difficult or impossible. However, the templated formation of nanocrystals which bind to a template in selected ratios based on the affinity to the binding sites rather than based on lattice matching or other constraints permits material having different lattice constants and different properties to be combined into a digital alloy. Accordingly, in one embodiment the digital alloy of the solar cell of FIG. 12A may include materials whose lattice constants are spaced greater than 0.3 Å to 0.5 Å apart from each other (see the chart in FIG. 1), or in some instances greater than 1 Å apart from each other and yet still be provided in the same layer of a digital alloy in the semiconductor material formed using templates according to the present invention.

FIG. 12B illustrates a different construction of a solar cell according to another embodiment. In this construction, electrodes 182 are on the top and bottom of the cell 174 of electrodes 184 are in between respective layers 186, 187, and 188. In the solar cell of FIG. 12B, the top layer 186 may be a standard binary material, such as GaN under which are two or more layers 187 and 188 having different bandgap properties than the uppermost layer 186. The operation of the various layers in FIGS. 12A and 12B is illustrated in FIG. 13.

Figure 13:
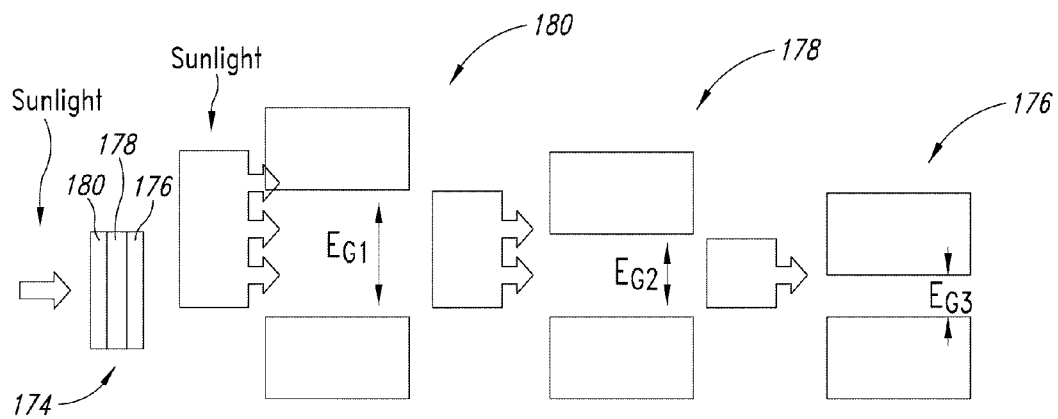
FIG. 13 illustrates schematically the various bandgaps of materials in a solar cell.

A solar cell represented schematically as 174 has sunlight impinged thereon, as shown in FIG. 13. The sunlight has multiple frequencies across a wide spectrum. The topmost material 180 has a first bandgap $E_{G1}$ and produces electricity at a first efficiency based on the frequency to which it is tuned for the sunlight. The second material 178 has a specifically tuned bandgap $E_{G2}$ in order to extract energy from a different frequency spectrum than the material 180. This bandgap $E_{G2}$ is therefore effective to generate additional electricity, greatly boosting the overall efficiency of the solar cell 174. Subsequent layers, one or more, represented as 176 have a different bandgap, in this embodiment less than the bandgaps of the layers 180 and 178, and generate electricity based on different parts of the spectrum, further boosting the overall efficiency of the solar cell 174. Electricity can be generated to a load 190 shown in FIG. 12B, and similar circuits can be placed on the solar cell of FIG. 12A being attached to electrodes 182, the load not being shown for simplicity.

Figure 14:
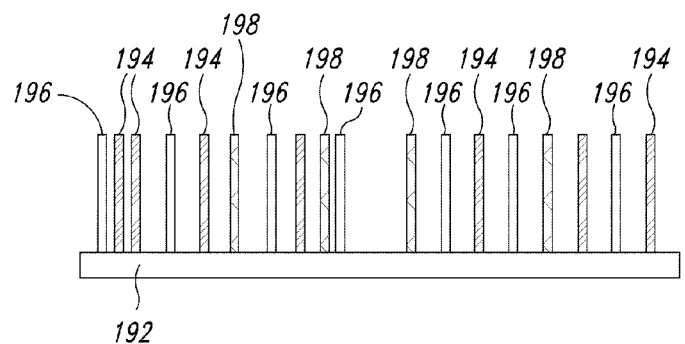
FIG. 14 illustrates schematically, various nanorods on a template according to the invention.
Figure 15:
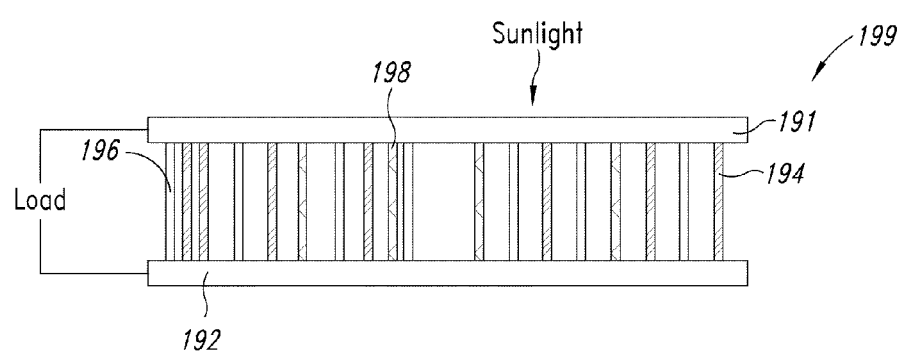
FIG. 15 illustrates schematically the nanorods of FIG. 14 used in an optoelectronic device.

FIG. 14 illustrates nanocrystals in the form of a plurality of nanorods which may be used according to principles disclosed herein. A substrate 192 can be provided as a template using the techniques explained herein. The nanocrystals are formed from various nanorods, each having different optoelectrical properties. A first plurality of nanorods 194 has a first bandgap. A second plurality of nanorods 196 has a second bandgap, while a third plurality of nanorods 198 have a third bandgap. Specific binding sites for each of these nanocrystals are provided on the template 192. The template 192 therefore has, on the single template, a large variety of nanorods each having different optoelectrical properties adjacent to each other. One of the uses of such a composition is shown in FIG. 15 in which the template 192 is impregnated within a conductive material so as to act as an electrode in a solar cell. A top electrode 191 may also be provided. Sunlight impinging upon the composition 151 will generate electricity separately from each of the different nanorods 194, 196, and 198. Each of these nanorods are custom engineered to have a different bandgap and thus generate electricity from different portions of the sunlight spectrum.

Accordingly, a single layer of material can be formed to provide very efficient solar cells. This layer of material can be incredibly thin, since the nanorods are in the nanocrystal range. In some embodiments, the nanocrystals which form the nanorods 194, 196, and 198, have widths in the range of 6-10 nanometers and lengths in the range of 500-800 nanometers. Such dimensions correspond to those of templates based on biological viruses, such as the M13 or phages which have been discussed herein and disclosed in the articles which are incorporated by reference. Accordingly, a solar cell 199 can be provided having a total thickness of less than 1,000 nanometers which is capable of producing electricity from sunlight using all of the frequencies available in the sunlight spectrum. If it is desired to further improve the efficiency, additional types of nanocrystals, in the form of nanorods having different bandgaps, can be provided parallel to those shown in FIGS. 14 and 15, each group of the nanorods absorbing sunlight from different frequencies of the spectrum and producing electricity based on that absorbed. A further advantage of the structure of FIGS. 14 and 15 is that all of the sunlight impinges equally on each of the nanorods without having to pass through various layers before reaching a bottom-most layer. Accordingly, even greater efficiencies for the production of electricity can be obtained using the structures of FIGS. 14 and 15.

2. Lithium Ion Batteries

Figure 18:
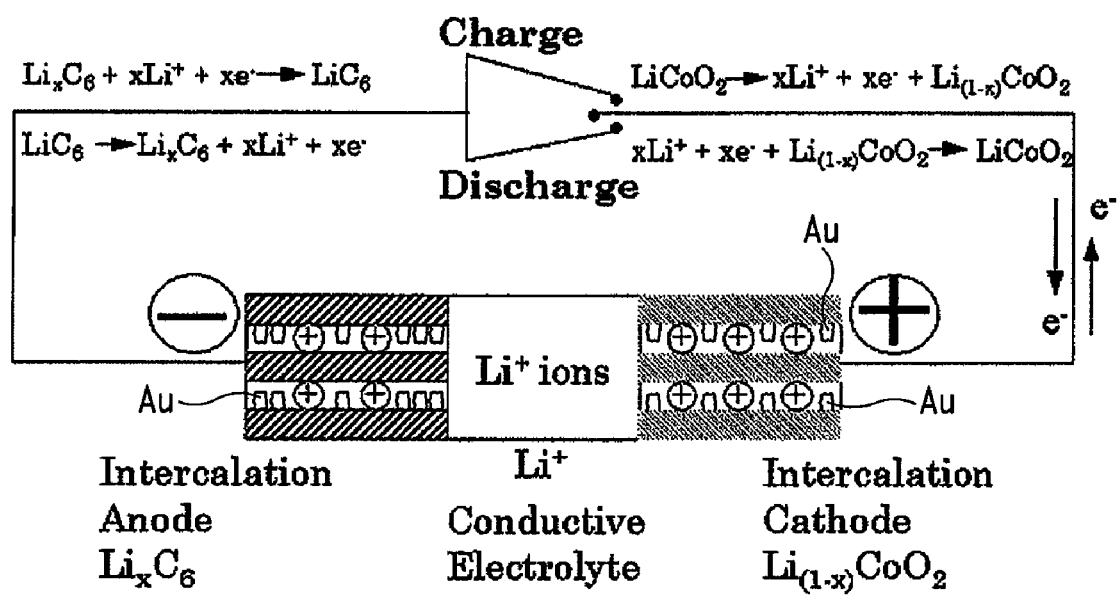
FIG. 18 illustrates a lithium ion battery having gold elements at selected locations in the anode or cathode according to principles of the present invention as illustrated in FIGS. 16 and 17.

A further use of the digital alloys according to the present invention is in lithium ion batteries, shown in FIGS. 16-18. A lithium battery has an anode and a cathode, the cathode usually including carbon in various graphite forms having lithium atoms intercalated therein and an anode which generally includes Co, Mn, O or some other metal oxide. It would be advantageous to have lithium ion batteries with substantially lower resistance and higher production capability over a longer life. One of the difficulties is that the materials currently used have limited conductivity and the properties which are conducive to use as an anode or cathode in a lithium ion battery are not conducive to low-resistance transfer of current.

According to the embodiments disclosed herein, a digital alloy can be formed having a highly conductive metal added to the cathode, or alternatively the anode or both, in a lithium ion battery to drastically increase the conductivity, the current production, and the operating lifetime of the lithium ion battery.

Gold (Au) is a highly conductive metal. If too many Au atoms or nanocrystals of Au are provided in the cathode or anode, the lithium ion battery operation will be impaired. Using currently known construction and alloy techniques, it is very difficult to add just a few atoms of a metal, such as Au, and have it be properly spaced and at the correct ratio so as to increase the conductivity without interfering with the electrical production capabilities of the battery. For example, it is known to produce a molecule of AuCo. However, if all of the Co in the battery is bound up to a corresponding Au atom, the operation of the lithium ion battery is substantially impaired.

According to principles taught herein, a selected ratio of Au to Co can be provided which will substantially increase the conductivity and current production capabilities of the battery without impairing the operational characteristics of the lithium battery. FIG. 16 illustrates a template 202 having a selected ratio of binding sites for nanocrystals of Au and nanocrystals of Co. The ratios are selected to have very few nanocrystals of Au so as to provide increased conductivity without interfering with the operation of the battery.

FIGS. 16 and 17 illustrate two different templates 202 which may be used as a substrate having an affinity for different nanocrystals of single elements. In the example of FIGS. 16-18, the substrate 202 is formed having a protein having an affinity for Co at regions 206 and a protein having an affinity for Au at regions 204. The regions 206 and 204 are linked to each other to form a continuous template 202. The ratio of the regions 206 and 204 are selected to specifically obtain a desired alloy in the final composition. Whereas, it may be difficult to provide a compound or alloy having a specific ratio of Co to Au in the metallurgical arts, using the template 202 having different proteins which attract and have an affinity for nanoparticles of the particular elements is able to achieve the construction of an AuCo having engineered ratios of a specific desired amount. In the example of FIG. 16, the ratio is approximately 6:1 of Co to Au whereas a different ratio is easily obtainable using different lengths for the proteins, as shown in FIG. 17.

FIG. 18 illustrates a lithium ion battery having a reduced resistivity of the electrode by the introduction of highly conductive gold atoms at particular locations in the membrane. These gold atoms are attached into the membrane using engineered proteins as has previously been described.

In the example of FIGS. 16 and 17, the template 202 binds to nanocrystals made of a single element. The single element can be a metal such as Au, Ag, Co, Li, C, or any one of the many semiconductors. Templates can also be constructed which have binding sites for individual elements at some locations and for binary compounds at other locations so as to provide selected ratios of ternary compounds which could not be obtained using standard alloy and/or molecule combination methods.

3. LED

Another embodiment of this invention would involve improved color control for light emitting diodes (LEDs).

Conventional LEDs are manufactured from bulk semiconductor compounds or organic compounds, such as small-molecule light emitting devices (SM-LED) or polymer light emitting devices (PLED). Such LEDs have an emissive region in which electron-hole radiative recombination occurs and thereby emits light. The emissive region is typically a junction region doped with impurities.

Figure 19:
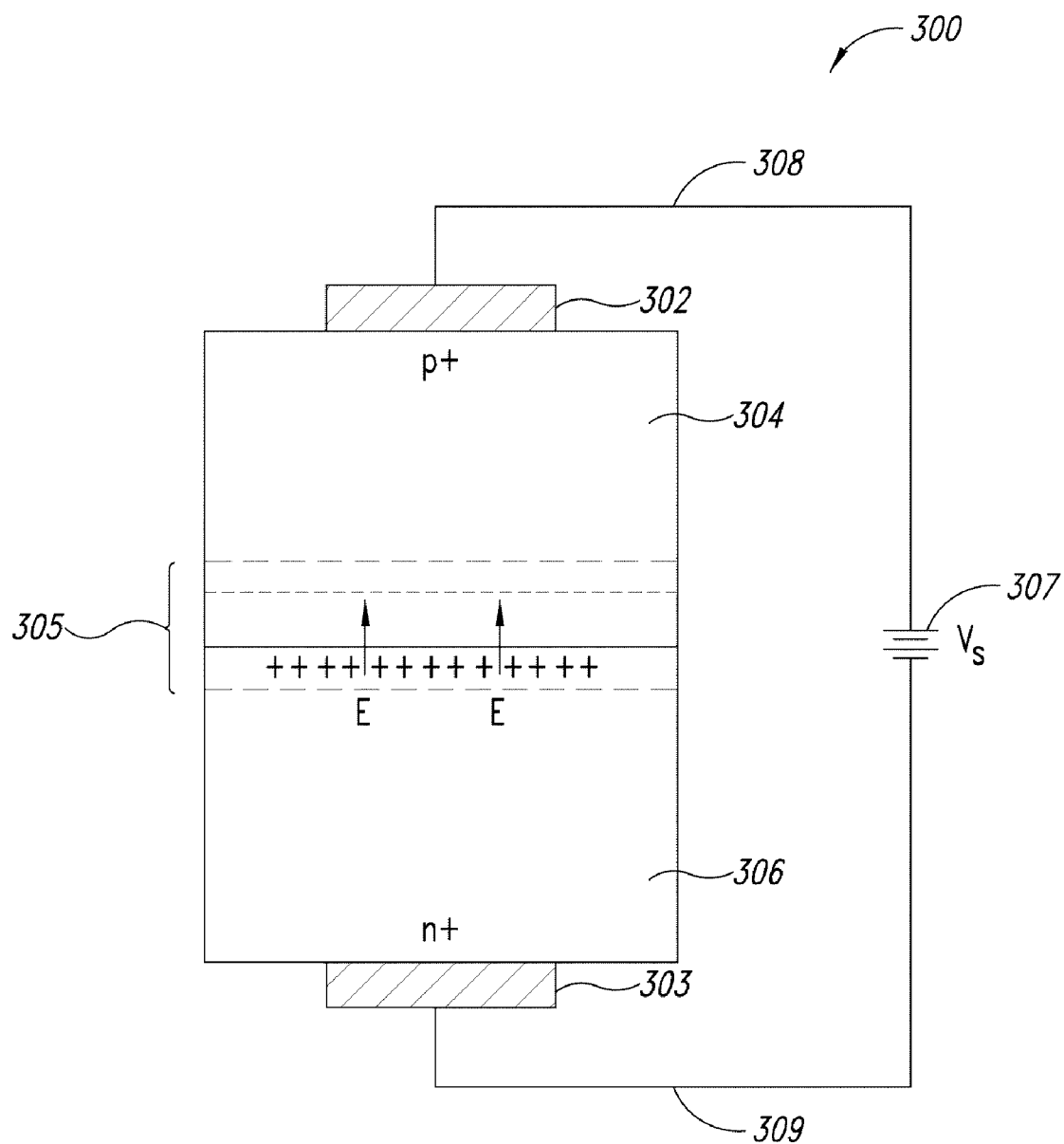
FIG. 19 illustrates a conventional LED device manufactured of a semiconductor material.

For example, FIG. 19 illustrates a conventional LED device 300 manufactured of a semiconductor material. The device has an anode 302, a cathode 303, a p-carrier transport region 304, an emissive region 305, an n-carrier transport region 306, a voltage source 307 and conducting leads 308 and 309 for electrically connecting the voltage source 307 to the device 300. The p-carrier region 304 is implanted or diffused with acceptor impurities creating a doped p+ region, and the n-carrier region 306 is implanted with donor impurities to create a doped n+ region. The emissive region 305 is a depletion region created proximate the p-n junction (i.e., the junction of the p+ region and the n+ region).

In operation, a user applies a source voltage that forward biases the p-n junction. Holes and electrons recombine in the emissive region 305 (i.e., the depletion region) to generate light. That is, electrons in the conduction band combine with holes in the valence band to generate photons, a majority of which have energy near or equal to the semiconductor bandgap energy. For example, if the energy gap is $E_g$ (i.e., $E_g=E_c-E_v$), then photons of wavelength $\lambda=hc/E_g$ are predominately generated. Since the conduction band is comprised of a near-continuum of energy states, the emissive layer generates a spectrum centered about the wavelength associated with the energy gap.

Organic LEDs are doped with impurities to create the emissive layer. These impurities, however, whether provided by implantation or diffusion, add additional processing steps and increase the risk of lattice damage. Lattice damage reduces the efficiency of the light emitting diodes by providing trapping sites for electrons and holes, increasing the probability of non-radiative recombination of electron-hole pairs, reducing the mobility of majority charge carriers, and modifying energy band structures in unpredictable ways. Lattice damage may also increase the spectral bandwidth of emitted light, resulting in less saturated colors. In addition, oxygen and water chemically degrade organic LEDs, thus reducing their useful lifetime. Furthermore, processing complications and physical restrictions limit the ability to manufacture organic LEDs with precisely defined emission wavelengths.

Nanoparticle light emitting devices generate light in a narrow spectrum due to quantum-constraints imposed upon the electronic wave functions. Such light emitting devices may also be color-tuned in manufacture by adjusting nanoparticle size or spacing between nanoparticles when arranged in an array. The energy bandgap of nanoparticle arrays can also be engineered by fabricating an array composed of nanoparticles of different semiconductor compounds. In operation, a non-doped nanoparticle semiconductor is injected with electrons and holes. Radiative recombination of electron-hole pairs generate photons with wavelengths dependent upon the engineered bandgap of the nanoparticle array.

As discussed above, nanoparticles (also referred to as quantum dots and nanocrystals) are intermediate in size between individual atoms and macroscopic material (i.e., material comprising millions of atoms and exhibiting macroscopic electrical, mechanical, and optical behavior). A typical nanoparticle may be composed of tens to hundreds of atoms. Nanoparticles thus exhibit electrical properties having both atomic and macroscopic characteristics. The electrical properties of nanoparticles depend upon the size and composition of the nanoparticle, the distance between nanoparticles when arranged in a patterned array (also referred to as the pitch of the array), and the proportions of nanoparticles of different composition when arranged in an array.

For example, a nanoparticle may be composed of approximately 50 molecules of GaAs. The GaAs nanoparticles (also generically referred to as binary nanoparticles) may be placed 1-2 nm apart to form a 2-D nanoparticle array with a 1-2 nm pitch. Or alternatively, the 2-D array may include approximately 20% GaAs nanoparticles and approximately 80% AlAs nanoparticles having electrical properties characteristic of the tertiary compound $Ga_{0.2}Al_{0.8}As$. Another 2-D array may be comprised of GaN and AlAs nanoparticles having electrical properties characteristic of the quaternary compound $Al_xGa_yAs_zN$ (wherein x+y+z=1).

Figure 20:
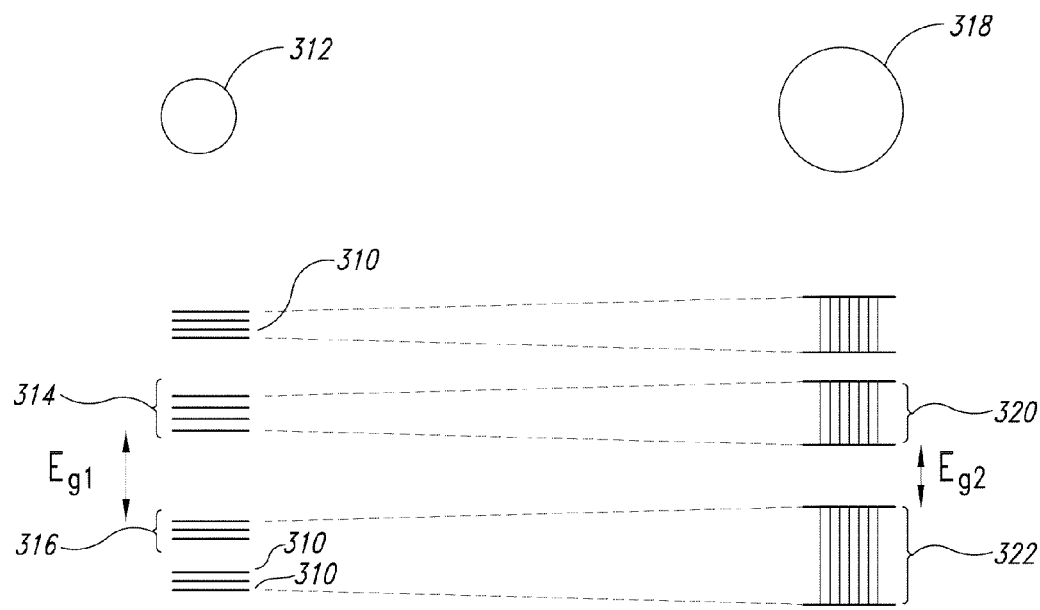
FIG. 20 shows the available energy states for individual nanoparticles.

For a nanoparticle of a specific size and composed of a given semiconductor material, FIG. 20 schematically illustrates the available electronic energy states. The left side of FIG. 20 shows the available energy states 310 for a single nanoparticle 312. The nanoparticle 312 is electrically isolated from other nanoparticles. Although the energy states are discrete and exhibit atom-like characteristics, the energy states are spaced closer together than states typically found in a single atom. In addition, groups of energy states are located in discrete energy bands. The discrete band 314 and the discrete band 316 are separated by an energy gap $E_{g1}$. The nanoparticle 312 exhibits both macroscopic properties (i.e., energy gap $E_{g1}$ and discrete energy bands 314 and 316) and atomic properties (i.e., discrete energy states 310).

The right side of FIG. 20 shows the energy state structure of a nanoparticle 318 that is larger than the nanoparticle 312. As a nanoparticle becomes larger in size, the electronic wave functions become less spatially confined. Electronic wave functions overlap with each other, causing the discrete energy levels to move closer together and form redundant energy states while broadening the energy bands. In effect, as the nanoparticle becomes larger, the discrete energy bands 314 and 316 (i.e., the narrow bands containing discrete energy states) become continuous energy bands 320 and 322 (i.e., broader energy bands containing a near-continuous number of available states described by a density of states function). As the energy bands broaden and contain a more continuous distribution of energy states, the energy gap decreases. As illustrated, the energy gap $E_{g2}$ between the energy bands 320 and 322 is smaller than the energy gap $E_{g1}$ between the energy bands 314 and 316. Thus, the size of the nanoparticle controls the size of the energy gap.

When electrons and holes in the nanoparticle combine, assuming the nanoparticle is comprised of a semiconductor material that allows for radiative recombination, a photon of wavelength $\lambda=K/E_g$ is generated, where K=hc and h is Plank's constant and c is the velocity of light in vacuum. Thus, nanoparticle sizes may be engineered to generate light of any wavelength.

Figure 21:
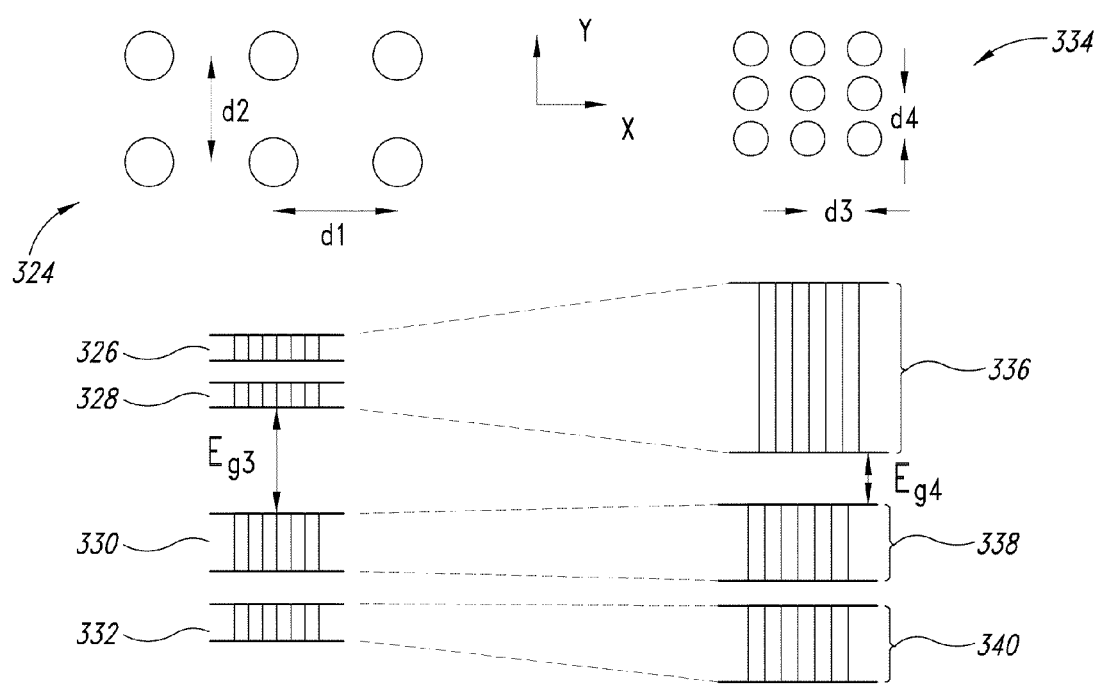
FIG. 21 shows the energy level structures for arrays of nanoparticles having different pitches.

For an array of nanoparticles of a specific size, pitch, and semiconductor material, FIG. 21 schematically illustrates the available electronic energy states. The left side of FIG. 21 shows the energy level structure for an array of nanoparticles 324 regularly spaced apart a distance d1 along an X-axis and a distance d2 along a Y-axis, where the X-axis is orthogonal to the Y-axis. The distances d1 and d2 may be different or the same. Both d1 and d2 refer to the pitch of the array. The energy level structure comprises a series of narrow, continuous energy bands 326, 328, 330 and 332. Each energy band is comprised of a near-continuous distribution of states described by a density of state function. The upper-level energy bands 326 and 328 are separated from the lower-level energy bands 330 and 332 by an energy bandgap $E_{g3}$. When an electron located in the upper band 328 radiatively recombines with a hole located in the lower energy band 330, a photon of energy $E=E_{g3}$ is generated.

The right side of FIG. 21 illustrates an energy level structure for an array of nanoparticles 334 having a pitch d3 and d4 that is smaller than the pitch d1 and d2 of the array of nanoparticles 324 of the left side of FIG. 21. The energy band structure includes one continuous upper band 336 and two continuous lower bands 338 and 340. As the nanoparticles of array 324 are moved closer together to create the nanoparticle array 334, the two narrow upper level bands 326 and 328 merge to generate the broad upper level band 336. In addition, the two lower level bands 330 and 332 have broadened to generate the lower bands 338 and 340, respectively. In the process of moving the nanoparticles closer together, the energy gap has deceased from $E_{g3}$ to $E_{g4}$. Thus, by changing the pitch of the nanoparticle array, the wavelength of light emitted as a result of radiative recombination of electrons and holes contained within each of the nanoparticles of nanoparticle array 324 can be modified. For example, if photons of a longer wavelength are desired, then the pitch of the array of nanoparticles is decreased. If photons of a shorter wavelength are desired, than the pitch is increased.

Figure 22:
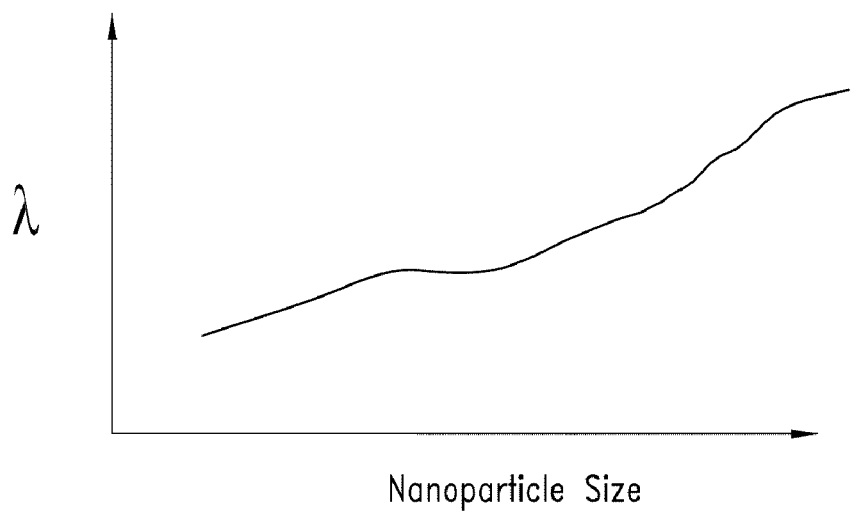
FIG. 22 illustrates the dependency of wavelength of light emitted from a nanoparticle on the size of the nanoparticle.

FIG. 22 illustrates the dependency of wavelength emitted from a nanoparticle upon the size of the nanoparticle. The energy gap of the nanoparticle decreases as the size of the nanoparticle increases. Thus, the wavelength of light emitted by the radiative recombination of holes and electrons in the nanoparticle increases as the nanoparticle size increases.

FIG. 22 illustrates the dependency of wavelength emitted from an array of nanoparticles upon the pitch of the array. The energy gap of the array of nanoparticles increases as the pitch of the nanoparticle array increases. Thus, the wavelength of light emitted by the radiative recombination of holes and electrons decreases as the pitch of nanoparticle array increases.

Figure 23:
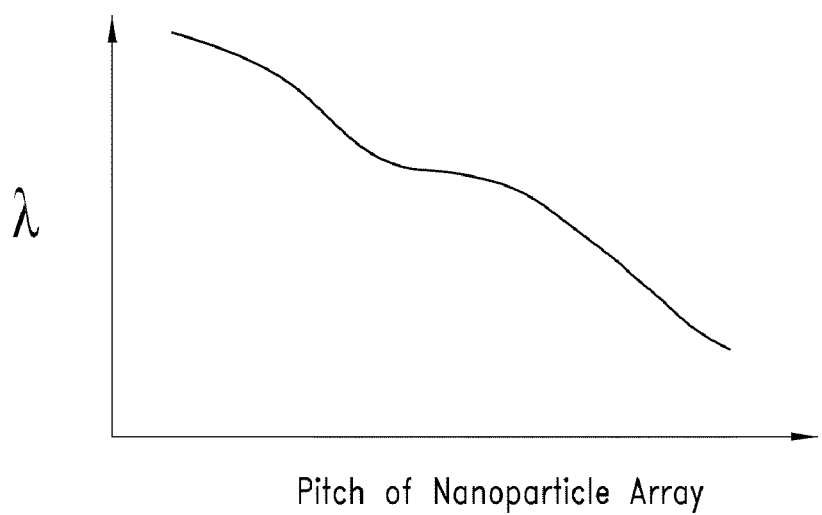
FIG. 23 illustrates the dependency of wavelength of light emitted from an array of nanoparticles on the pitch of the array.

FIGS. 22-23 are illustrative of the general dependencies of wavelength upon nanoparticle size and pitch of a nanoparticle array, but the dependencies are not intended to be exact or exclusive. One of skill in the art will appreciate that the wavelength depends upon at least the following four variables: nanoparticle size, pitch of an array of nanoparticles, composition of individual nanoparticles, and whether the array of nanoparticles includes a blend of individual nanoparticles of different composition. One of skill in the art will recognize that these four variables may be combined in various ways to generate light of any wavelength from a nanoparticle array.

Figure 24A:
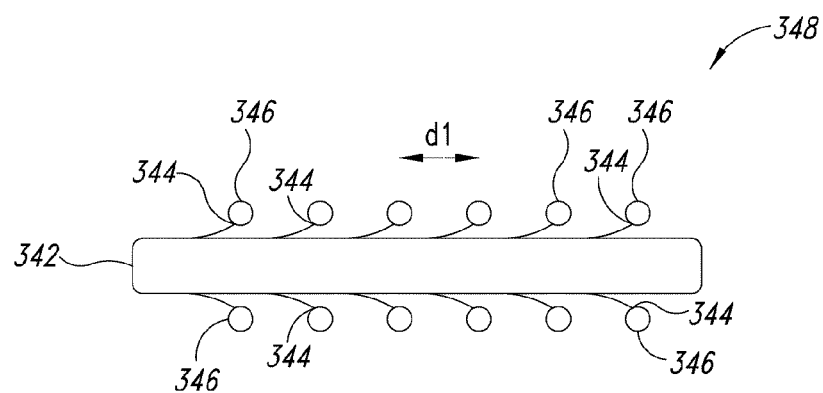
FIG. 24A illustrates a template having a plurality of binding sites for binding GaAs nanoparticles of a first size to generate an array of nanoparticles of pitch d1.

FIGS. 24A-24D illustrate templates for binding a plurality of nanoparticles. For purposes of illustration and ease of discussion, it is assumed that each binding site has an affinity for a specific nanoparticle, such as a GaAs nanoparticle. However, embodiments include templates for binding nanoparticles of any composition and size. FIG. 24A illustrates a template 342 having a plurality of binding sites 344 for binding GaAs nanoparticles 346 of a first size to generate an array 348 of nanoparticles of pitch d1, according to one embodiment.

Figure 24B:
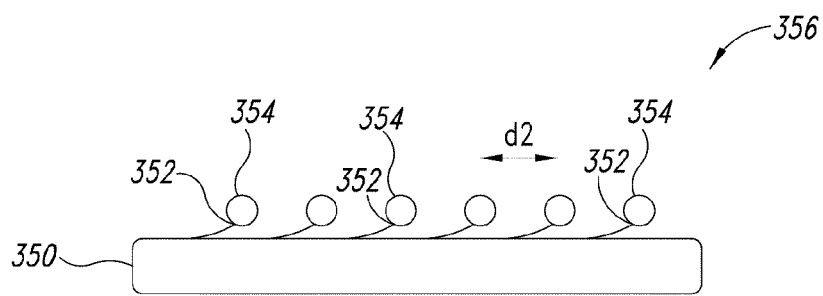
FIG. 24B illustrates a template having a plurality of binding sites for binding GaAs nanoparticles of a second size to generate an array of nanoparticles of pitch d2.

FIG. 24B illustrates a template 350 having a plurality of binding sites 352 for binding GaAs nanoparticles 354 of a second size to generate an array 356 of nanoparticles of pitch d2, according to a second embodiment. As illustrated, the nanoparticles 354 are larger than nanoparticles 346. Furthermore the pitch d2 of the nanoparticle array 356 established by template 350 is smaller then the pitch d1 of the nanoparticle array 348 established by template 342. In other words, template 350 has been engineered to establish the array 356 of nanoparticles that generate light of a longer wavelength than light emitted by the array 348 of nanoparticles.

Figure 24C:
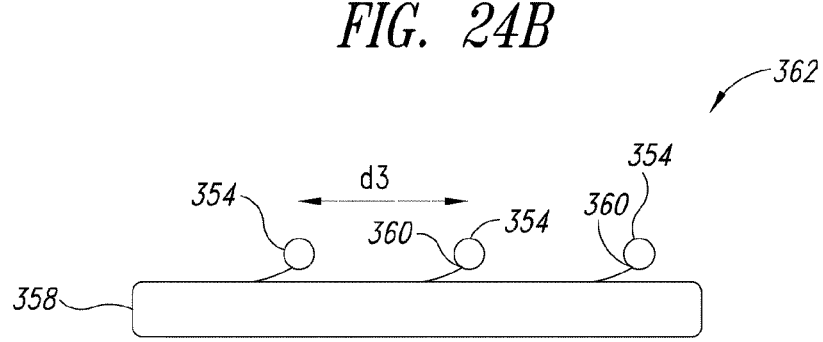
FIG. 24C illustrates a template having a plurality of binding sites for binding GaAs nanoparticles of the second size to form an array of nanoparticles of pitch d3.

FIG. 24C illustrates a template 358 having a plurality of binding sites 360 for binding GaAs nanoparticles 354 of the second size to form an array 362 of nanoparticles of pitch d3, according to a third embodiment. The pitch d3 of the array 362 of nanoparticles is larger than the pitch d2 of the array 356 of nanoparticles of FIG. 24B. Consequently, the template 358 has been engineered to form the array 362 of nanoparticles that generate light of a shorter wavelength than the light emitted by the array 356 of nanoparticles.

Figure 24D:
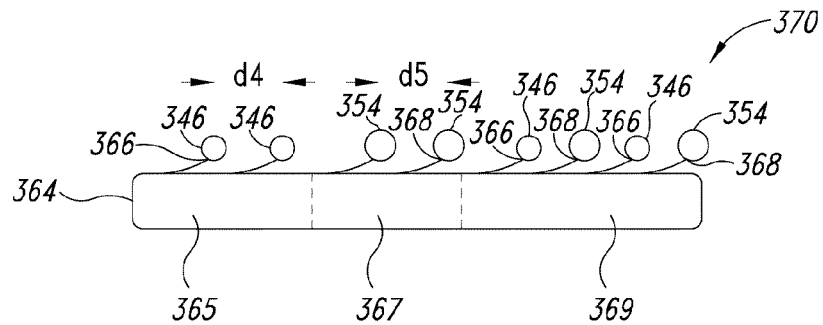
FIG. 24D illustrates a template having a first plurality of binding sites for binding GaAs nanoparticles of the first size and a second plurality of binding sites for binding GaAs nanoparticles of the second size to generate an array of nanoparticles of multiple pitch d4, d5 and d6.

FIG. 24D illustrates a template 364 having a first plurality of binding sites 366 for binding GaAs nanoparticles 346 of the first size and a second plurality of binding sites 368 for binding GaAs nanoparticles 354 of the second size to generate an array 370 of nanoparticles of plural pitches d4, d5 and d6, according to a fourth embodiment. Template 364 is engineered to generate light of at least three different wavelengths. For example, a portion 365 of the template 364 has an associated nanoparticle size and pitch d4 for generating light of a first wavelength, a portion 367 of the template 364 has an associated nanoparticle size and pitch d5 for generating light of a second wavelength, and a portion 369 of the template 364 has an associated nanoparticle size and pitch d5 for generating light of a third wavelength. Whether or not a particular portion of the template generates light of a measurable wavelength and intensity depends upon the number of nanoparticles that comprise the portion of the template. FIG. 24D shows only a few nanoparticles for each portion 365, 367 and 369 of the template 364 for ease of illustration. However, any number of nanoparticles in each portion 365, 367 and 369 of the template 364 could be employed to generate light of a desired intensity and wavelength.

In one embodiment, templates 342, 350, 358 and 364 are biological templates (i.e., organic templates), including folded-protein templates including specifically engineered binding sites arranged in 2-D array having affinities for nanoparticles of specific sizes and composition. Exemplary embodiments of the biological templates are discussed herein.

According to another embodiment, templates may be engineered that bind nanoparticles of different compositions to create a multi-compositional nanoparticle array having electrical properties of ternary and quaternary compounds, for example. These multi-compositional nanoparticle arrays may be manufactured to generate light of a desired wavelength while reducing lattice imperfections that otherwise reduce efficiency, switching frequency, spectral purity and intensity of the emitted light.

Figure 25:
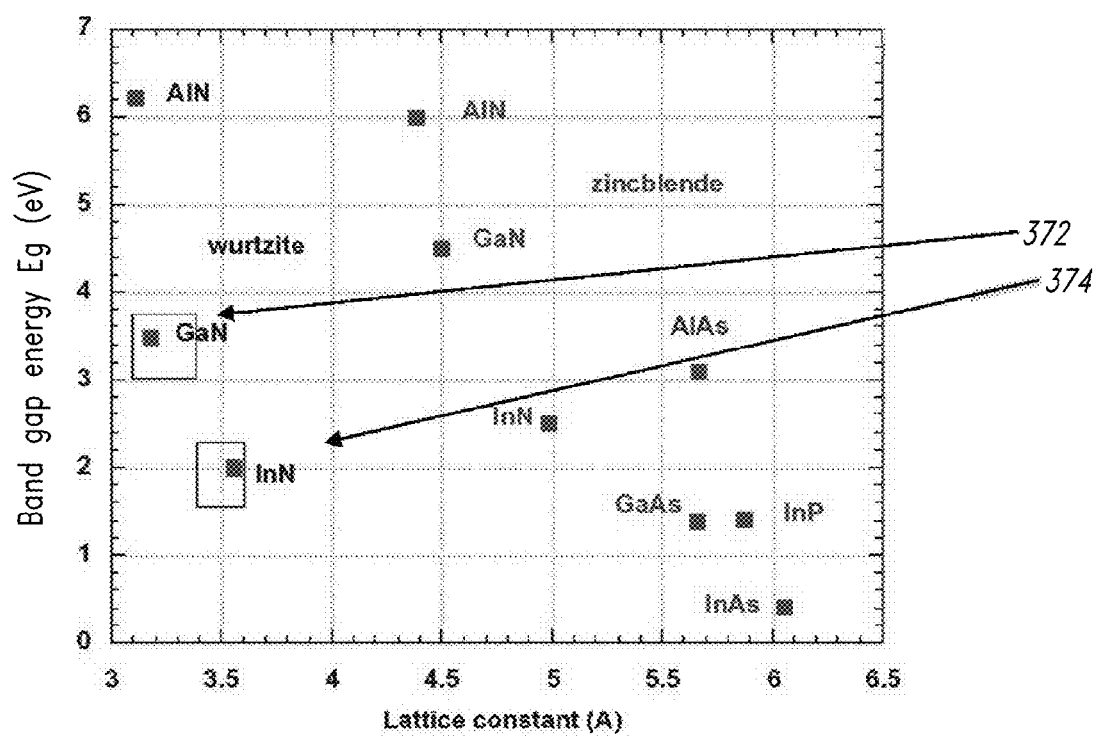
FIG. 25 illustrates the band gap energy and lattice constant for various binary compounds.

As shown in FIG. 25, two particular materials, GaN and InN labelled 372 and 374, respectively, being formed of a Wurlitzer-type crystalline structure, have respective bandgaps of 3.5 and approximately 2 electron volts. Each of these materials are binary compounds of nanocrystalline components.

Referring back to FIG. 3, a conduction band 20 and a valence band 21 for GaN and a conduction band 22 and a valence band 23 for InN. When electrons and holes are injected into a material made of the GaN compound, the compound emits light at a certain wavelength. Whereas, when electrons and holes are injected into a material made of the InN compound, the InN emits light of a different wavelength. It may be considered that GaN is an example of a binary compound of the structure AB and the InN is another acceptable binary compound having one element in common with that of the prior compound and thus being denoted by the symbol CB. Each of the binary compounds has a known conduction band and valence band as illustrated in FIG. 3.

The two binary components AB and CB, in this first example GaN and InN, are assembled onto a common template in order to obtain a material having a bandgap intermediate between that of AB and CB. In particular, a new material (i.e., a semiconductor alloy) is formulated having the properties of a ternary compound that includes indium of a selected ratio, gallium of a selected ratio, and nitrogen of a selected ratio by engineering the template to which the binary compounds are affixed. Accordingly, shown in FIG. 3 a bandgap E having a value corresponding to $In_xGa_{1-x}N$ is achievable.

FIG. 26 illustrates the formation of a semiconductor alloy $In_xGa_{1-x}N$ by combining InN and GaN in a suitable stoichiometric ratio (similar to that of combining GaAs and AlAs illustrated in FIG. 7). More specifically, FIG. 26 illustrates a template 388 which has been engineered having the desired ratio of a material which emulates a ternary compound of $Ga_xIn_{1-x}N$. The template 388 has a first plurality of binding sites 390 which have an affinity for GaN 394. The template also contains a second plurality of binding sites 392 which have an affinity for InN 396. The ratio of the first binding sites 390 to the second binding sites 392 is selected to achieve a desired result. The template 388 is then exposed to a fluid having a plurality of nanoparticles of the binary compound GaN. The GaN nanoparticles 394 affix themselves to the respective binding sites 390 of the template 388 and do not affix or attach to the binding sites 392. The template 388 is also exposed to a fluid having InN nanoparticles therein and the InN nanoparticles 396 affix themselves to the binding sites 392. In some embodiments, it is desired to have the fluids in separate liquid solutions and the template 388 is sequentially exposed to the fluids, while in other embodiments, the template 388 may be exposed simultaneously to a single liquid solution having both binary components therein.

The binary nanocrystal components which are to form the digital alloy can have any desired element composition. In the example provided for FIG. 26, the binary components are InN and GaN. Any acceptable binary component can be used for which a binding site to the template 388 is readily available. It is desired that the binding sites be close enough to form a continuous material from a chemical and electrical point of view. The binding sites should be sufficiently spaced that the nanoparticles do not clump together. Namely, the binary nanoparticles should be in the form of nanocrystals which are placed in an orderly array.

The ratio of the binding sites 390 and 392 is selected to provide the desired number of the components of binary compound 1 and binary compound 2. Accordingly, template 388 is engineered which has the properties of different binding sites that can be uniquely attached to the correct nanoparticle and the binding sites spaced the correct distance apart from each other in order to provide the desired chemical and electrical properties as if it were a continuous material. Preferably, the binding sites have the spacing of a few nanometers from each other. When such a template is exposed to a solution having nanoparticles or nanoparticles composed of material which have an affinity to the respective binding sites, then the materials will bind to the template to form an ordered array of the material so that the final template 388 emulates a ternary compound having three different elements in respective ratios rather than two different binary compounds. The use of nanoparticles permits the formation of such materials which will emulate for physical, chemical, and electric purposes a ternary compound even though they are composed of two binary components.

Thus, one embodiment provides an LED including a light emitting material, which is an alloy formed by two materials: the first material is a compound represented by $A_mB_n$, the second material is a compound represented by $C_pD_q$ and the alloy can be represented by $(A_mB_n)_x(C_pD_q)_y$, wherein, A, B, C and D are elements of the Periodic Table; $0 \leq m \leq 1$;

$0 \leq n \leq 1$; m+n=1; and $0 \leq p \leq 1$; $0 \leq q \leq 1$; and p+q=1, provided that m and n are not 0 at the same time, and p and q are not 0 at the same time.

In certain embodiments, A, B, C and D are different from one another and the resulting alloy is a quaternary alloy.

In other embodiments, A, B and C are different from one another, and B is the same as D, and the resulting alloy is a ternary alloy.

In yet other embodiments, n=q=0, and the resulting alloy is a binary alloy $A_xC_y$, or $A_xC_{1-x}$ (as x+y=1).

As discussed herein, such an alloy can be formed based on a composition having biological templates which specifically bind to the first material or second material to achieve a desired stoichiometric ratio of the two component materials (see, also, FIGS. 10-11). More specifically, such a composition comprises a plurality of templates, each template comprising at least one first binding site and at least one second binding site, the first binding site having a specific binding affinity for a first nanoparticle of a first material, the second binding site having a specific binding affinity for a second nanoparticle of a second material, wherein the templates are selected to include, in percentages, x first binding sites and y second binding sites; a plurality of the first nanoparticles bound to respective first binding sites; a plurality of the second nanoparticles bound to respective second binding sites; wherein the templates are assembled such that the first material and the second material form an alloy at a stoichiometric ratio of x:y.

Thus, in a LED device including a light emission material based on the alloy described herein (e.g., a ternary compound resulted from two binary compounds), when electrons and holes are injected into the nanoparticles, light with a narrow-banded spectrum centered on the frequency associated with the ternary compound bandgap will be emitted.

Figure 27:
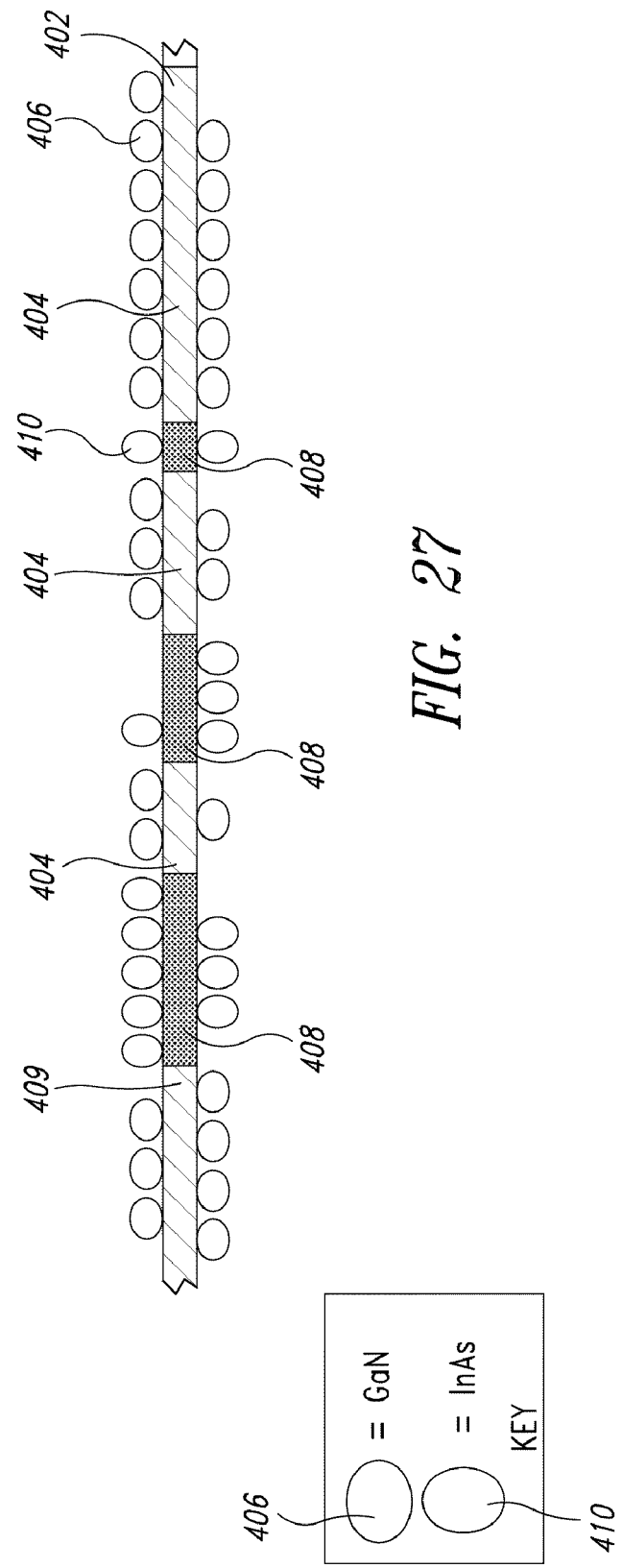
FIG. 27 illustrates a template that has been engineered for different binary compounds.

FIG. 27 illustrates a template that has been engineered for binding different binary compounds. As illustrated, a template 402 has a portion 404 which has been engineered to have an affinity for a given nanoparticle 406, in this case GaN. A different portion of the template 408 has been engineered to have an affinity for a different nanoparticle 410, in this case InAs. Different portions of the template 402 have been linked together to create a known ratio between the regions 404 and 408, the ratio being selected in order to obtain a desired end compound having electrical and chemical properties which are desired for a particular application.

By engineering the specific ratio of the areas of the template 404 and 408 which have an affinity for the respective different nanoparticles, the particular chemical and electrical properties of the end material can be specifically engineered. In the specific example shown in FIG. 27, the ratio is approximately 2:1, so that a quaternary compound having the properties of GaN in the 2:1 ratio of InAs are obtained. The regions 408 are unevenly spaced with respect to the regions 404.

As an example, the template 402 can be a protein (native or engineered) that contains peptide sequences that specifically bind to different nanocrystals. These peptide sequences correspond to the first and second binding sites. Thus, the arrangements and relative ratio between the peptide sequences can determine the stoichiometric ratio of the constituent nanocrystals and ultimately determine the alloy composition.

Figure 28:
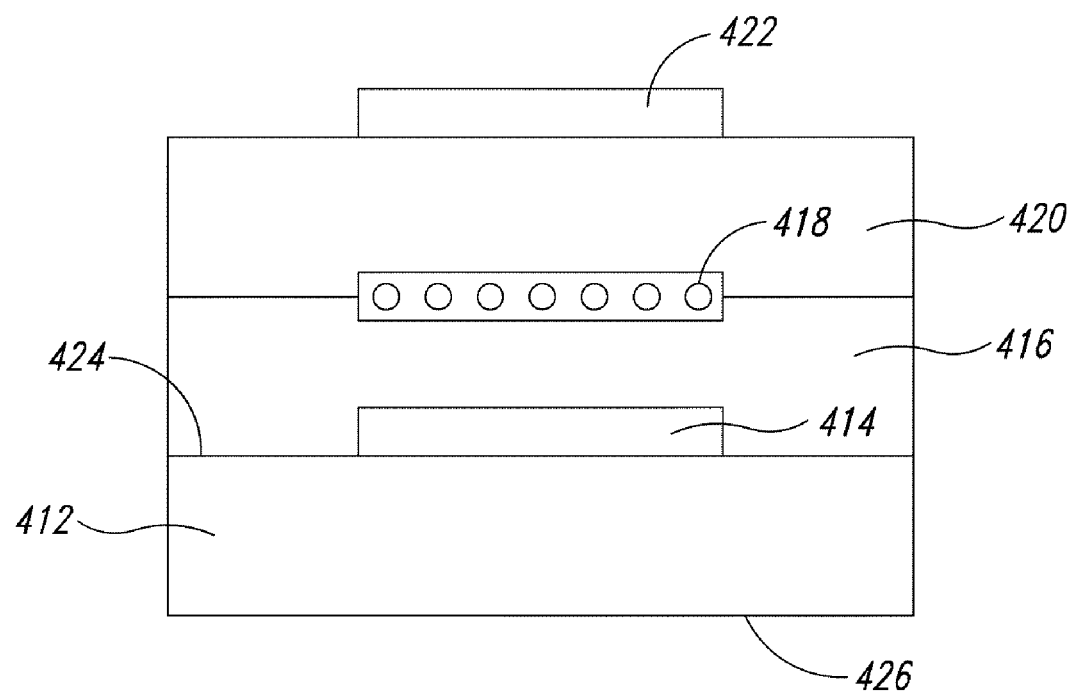
FIG. 28 illustrates a nanoparticle-based light-emitting device.

FIG. 28 illustrates a nanoparticle-based LED, according to one embodiment of the invention. The LED includes a substrate 412, a first injection contact 414, a first dielectric layer 416, a layer of nanoparticles 418, a second dielectric layer 420 and a second injection contact 422. External contacts (not shown) may be made to the first and second injection contacts 414 and 422. For example, a first external contact may include metal contacts deposited on a first surface of the substrate 424 and connecting with the first injection contact 414. Alternatively, vias (not shown) may be etched into the second surface 426 of the substrate 412 proximate the first injection contact 414. Metal may then be deposited in the vias to provide external contacts to the first injection contact 414. The process of attaching external contacts to metal injection pads is well known to one of skill in the art, and one may employ any of such methods of attaching external contacts to metal pads.

In operation, the injection contacts 422 and 414 are connected to an external voltage source (not shown) via the external contacts (not shown). One of the injection contacts is an anode, and the other injection contact is a cathode. For example, the first injection contact 414 may be an anode that injects holes into the first dielectric layer 416 and the second injection contact 422 may be a cathode that injects electrons into the second dielectric layer 420. One of skill in the art will appreciate that an injection of holes is equivalent to a withdrawal of electrons. For a given operational source voltage, typically less than 10 volts, a dielectric layer thickness is selected from a range of acceptable thicknesses. For example, in one preferred embodiment the dielectric thickness is in a range of 1 to 500 hundred nanometers and the operating voltage is in a range of 0.6 to 40 volts. A dielectric layer thickness is selected, given a specific operating voltage range, to facilitate quantum-tunneling of the electrons and holes through the first and second dielectric layers 416 and 420 into the nanoparticles without exceeding the breakdown voltage threshold of the dielectric. Once inside the nanoparticles, the electrons and holes radiatively recombine to generate photons with an energy equivalent to the engineered energy gap of the nanoparticle layer 418.

Since nanoparticles are much smaller than p-n junction regions of conventional LEDs, and since nanoparticles are not doped with impurities as convention p-n junctions of light emitting diodes, each nanoparticle is highly efficient in converting electrical energy into optical energy. That is, nanoparticles have fewer non-radiative mechanisms available for electron-hole recombination. For example, nanoparticles have fewer trapping sites associated with lattice imperfections that typically generate lattice vibrations (i.e., phonons) upon recombination of electrons and holes. In other words, nanoparticles are highly efficient at converting electrical energy into electromagnetic energy while reducing conversion of electrical energy into vibrational energy.

In addition, selection of a dielectric layer thickness to facilitate electron/hole transport via quantum-tunneling is important in keeping dielectric charge-carrier mobility high. The nanoparticle layer 418 may include any number of nanoparticles. For example, the nanoparticle layer 418 may be any of the nanoparticle arrays formed by the templates illustrated in FIGS. 24A-24D (i.e., templates 342, 350, 358 and 364), FIG. 26 (i.e., template 388), FIG. 10 (i.e. template 161), FIG. 11 (i.e., template 163), or FIG. 27 (i.e., template 402). In an alternate embodiment, the light emission layer (i.e., nanoparticle layer 418) includes only one nanoparticle.

Various methods can be employed to create the nanoparticle array layer 418. In some embodiments, the layer 418 is an array of nanoparticles, i.e., a two-dimensional (2D) orderly or regular arrangement of the nanoparticles, with or without their respective templates. In these embodiments, the nanoparticles may have substantially uniform or varying sizes, shapes and pitches. Advantageously, an array of uniform nanoparticles produces a dense and precise distribution of the nanoparticles.

In certain embodiments, the nanoparticles can self-assemble into the layer 418 by controlled evaporation of a colloidal suspension of the nanoparticles in a suitable solvent. Typically, lateral capillary forces provide the main driving force for the self-assembling behavior of the nanoparticles. Parameters such as the concentration of the suspension and the solvent evaporation rate can be controlled to arrange the nanoparticles into the array of a desirable density. If desired, surface pressure can be applied to assist the assembly of the nanoparticles into an array, such technique (e.g., Langmuir-Blodgett film formation) is well known to one skilled in the art.

In other embodiments, the nanoparticles can be directed by nano-sized templates to assemble into an array. As discussed herein, suitable templates can be any synthetic and natural materials that assemble into an ordered, two-dimensional nanoscale structure, which structure is capable of directing nanoparticles to align in a similarly ordered fashion. The nanoscale structure formed by a regular arrangement (or packing) of the templates is also referred to as a "template lattice". It should be understood that the template lattice can be crystalline or amorphous, with the former producing denser packing of the templates.

Typically, each template has a well-defined functional domain, which captures, anchors, nucleates or otherwise restrains a nanoparticle. Due to the structure of the template lattice, the functional domains are repeated with periodicity, which allows the nanoparticles to arrange with the same periodicity. The functional domain can be, for example, a cavity or pore, in which a nanoparticle can be at least partially entrapped or physically confined. In certain embodiments, in addition to, or independent of the physical confinement, the functional domain may also exhibit a binding affinity for the nanoparticle based on their respective chemical natures. The term "restrain" thus refers to both types of forces, i.e., physical confinement and chemical affinity, with which the templates can anchor the nanoparticles such that their arrangements are defined by the template lattice.

In certain embodiments, the templates can capture preformed nanoparticles. "Preformed nanoparticles" are prepared independently of the templates. In other embodiments, the templates can cause the nanoparticles to nucleate from a solution phase. As discussed herein, nucleation is a process of forming a nanoparticle in situ by converting a precursor in the presence of a template. Typically, the in situ generated nanoparticle binds to and grows at least partially within the functional domain of the template. Detailed description of forming nanoparticles by nucleation process can be found in, e.g., Flynn, C. E. et al., "Synthesis and Organization of Nanoscale II-VI Semiconductor Materials Using Evolved Peptide Specificity and Viral Capsid Assembly," (2003) *J. Mater. Sci.*, 13, 2414-2421; Lee, S-W et al., "Ordering of Quantum Dots Using Genetically Engineered Viruses," (2002) *Science* 296, 892-895; Mao, C. B. et al., "Viral Assembly of Oriented Quantum Dot Nanowires," (2003) *PNAS, vol.* 100, no. 12, 6946-6951, and US2005/0164515.

The shape of the template is typically symmetrical in order to promote tight packing. Examples of the suitable shapes include, without limitation: spheres, cylinders, rings, disks and the like. Moreover, the templates may be uniform or varying in their sizes, shapes and pitches. Typically, the lattice symmetry can be 2-fold (oblique), 4-fold (square), 3 or 6-fold (hexagon), in ascending order of density.

Figures 29A, 29B:
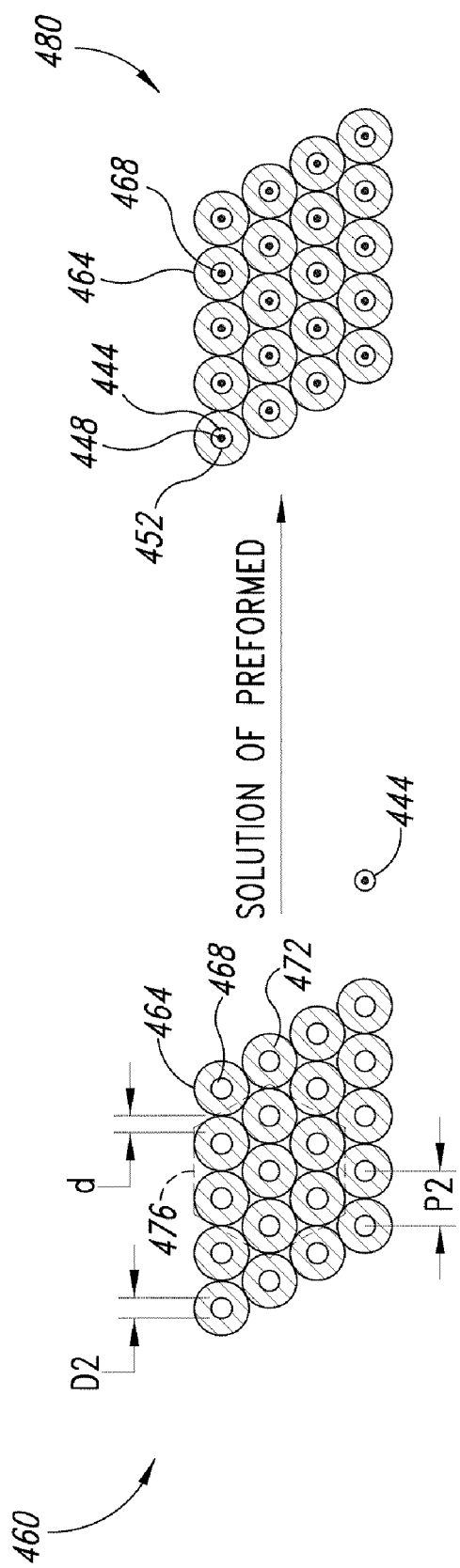
FIGS. 29A and 29B illustrate exemplary template lattice.

FIG. 29A illustrates one embodiment, in which templates 464 self-assemble into a template lattice 460 on a solid surface (not shown). Uniformly, each template 464 has a ring (e.g., donut-shaped) structure including a cavity 468 within a wall 472. The dashed outline 476 indicates a closely packed hexagonal structure of the template lattice 460. The diameter of the cavity is designated as D2. The thickness of the wall is designated as "d". The center-to-center spacing between two adjacent templates is designated as "P2". In a closely packed lattice (e.g., a hexagonal structure), P2 is substantially the same as twice the thickness of the wall 472 of the template 464 (P2=2*d).

In one embodiment, the template lattice 460 is contacted with a suspension of nanoparticles 444. The nanoparticles 444 are individually restrained (or anchored) by the cavities 468, thereby assembling into a similar lattice structure as the underlying template lattice. FIG. 29B illustrates schematically the assembly of nanoparticles 444 directed by the template lattice 460 to form a nanoparticle lattice 480. More specifically, the nanoparticles 444 of uniform diameters "D1" are restrained by the cavities 468 of the templates 464. According to the embodiment shown in FIG. 29B, D1 is substantially the same as D2 (D1=D2) and the nanoparticles 444 are completely confined in the cavities 468. In other embodiments, the structure of the template allows for certain degrees of elasticity and enables the cavity to be stretched to accommodate nanoparticles slightly larger than D2.

After the nanoparticles 444 have been positioned according to the template lattice, the nanoparticles remain in their positions when the underlying templates are removed. A nanoparticle array such as the array 480 (FIG. 29B) can be obtained. It is understood that the size and density of the nanoparticles 444 in the array 480 are determined by the overall size of the template, the size of its cavity, and the packing of the template.

In one embodiment, the center-to-center spacing between two adjacent nanoparticles "P1" in the nanoparticle array 440 is substantially the same as the center-to-center spacing between two adjacent templates "P2" (P1=P2). Advantageously, it is possible to obtain a nanoparticle array having a desired particle size and density by selecting the template having a cavity and wall of a suitable size.

Any of the biological templates discussed herein can be used to create the nanoparticle arrays suitable as the light emitting material. Such templates include, for example, natural material such as DNA, bacterial and archaeal surface layer proteins, globular proteins, virus capsids, and phage can self-assemble into ordered 2D structures and are examples of suitable templates, as defined herein. Synthetic materials such as bioengineered proteins and polymers are also suitable templates.

Using chaperonin 500 as an exemplary template, FIG. 30 shows its ring-shaped structure having nine subunits 504. An open pore 508 is positioned in the center of the chaperonin. Optionally, through genetic engineering, a binding site 512 may be present on each subunit. The binding site can be an amino acid or a peptide sequence that displays favorable affinity for certain nanoparticles. For example, a ring of nine cysteines can be present and exposed to the open pore 512, which can bind and anchor a gold or zinc nanoparticle of a comparable size to the open pore. Where the chaperonin is engineered to contain two or more different types of binding sites, two or more different types of nanoparticles can bind to the chaperonin template according to a desired ratio. As previously shown in FIGS. 5A, 5B and 6, alloys (e.g., tertiary or quaternary alloys) can be formed based on the compositions of the nanoparticles and their relative stoichiometric ratio.

Other suitable templates include, but are not limited to, a S-layer protein, apoferritin, *E. coli* DNA polymerase III β subunit, and a biological scaffold to which one or more peptide sequences have been fused, as discussed herein.

As noted above, pre-formed nanoparticles can be restrained by the functional domains of the templates through physical confinement and/or binding affinity. Thus, further described herein is a method comprising: assembling a plurality of templates into an ordered template lattice, contacting the template lattice with a plurality of nanoparticles, each nanoparticle having a conductive core and an insulating shell; and forming a nanoparticle array as defined by the template lattice.

In certain embodiments, such as shown in FIG. 31A, a fluid suspension 520 of nanoparticles 444 and templates 464 in a solvent can be prepared. A portion of the templates 464 may capture some nanoparticles in the solution phase; however, this process is not expected to be efficient. Moreover, in the solution phase, the template 464 may assume a relaxed form 464', which is not conductive for confining the nanoparticles, if physical confinement is the only form of restraint.

The fluid suspension 520 is then deposited on a solid surface 524. The solid surface can be a metal, metal alloy, semiconductor material (e.g., a channel region) and the like. As the solvent evaporates, the templates self-assemble into a 2D ordered structure 480 while simultaneously bind to the nanoparticles 444 (FIG. 31B). Thereafter, the templates 464 can be removed by, for example, annealing to provide the nanoparticle array 440 (FIG. 31C).

In another embodiment, the templates 464 can initially form into an ordered structure 460 on the solid surface 524 (FIG. 32A). As shown in FIG. 32B, the solid surface is then contacted with or floated on a suspension 528 of the nanoparticles 444 (i.e., sols). The solid surface 524 having the template lattice 460 can be washed and re-contacted with the suspension 528. This process can be repeated multiple times as needed to allow for the nanoparticles 444 to bind to the template lattice 460. Thereafter, a nanoparticle lattice 480 and a nanoparticle array 440 can be obtained (see, e.g., FIGS. 31B and 32C).

In other embodiments, nanoparticles can be nucleated in the presence of the templates. For example, a metal or metal alloy nanoparticle can be produced by a reducing a water-soluble metal salt (i.e., a precursor to the metal) in a suspension of the templates. Suitable reducing agents include without limitation, sodium borohydride, hydrazine hydrate and the like, see, e.g., U.S. Pat. No. 6,815,063. Preferably, the templates can control the growth of the nanoparticles by physically confining the nanoparticles in a cavity. Thereafter, the templates containing the metal nanoparticles can be assembled directly on a solid surface. Alternatively, the templates can be assembled into a 2D structure at a liquid-liquid interface (e.g., an MES/glucose subphase solution) followed by transferring the 2-D structure to a solid surface. See, e.g., U.S. Pat. Nos. 6,896,957 and 6,713,173.

Figure 33:
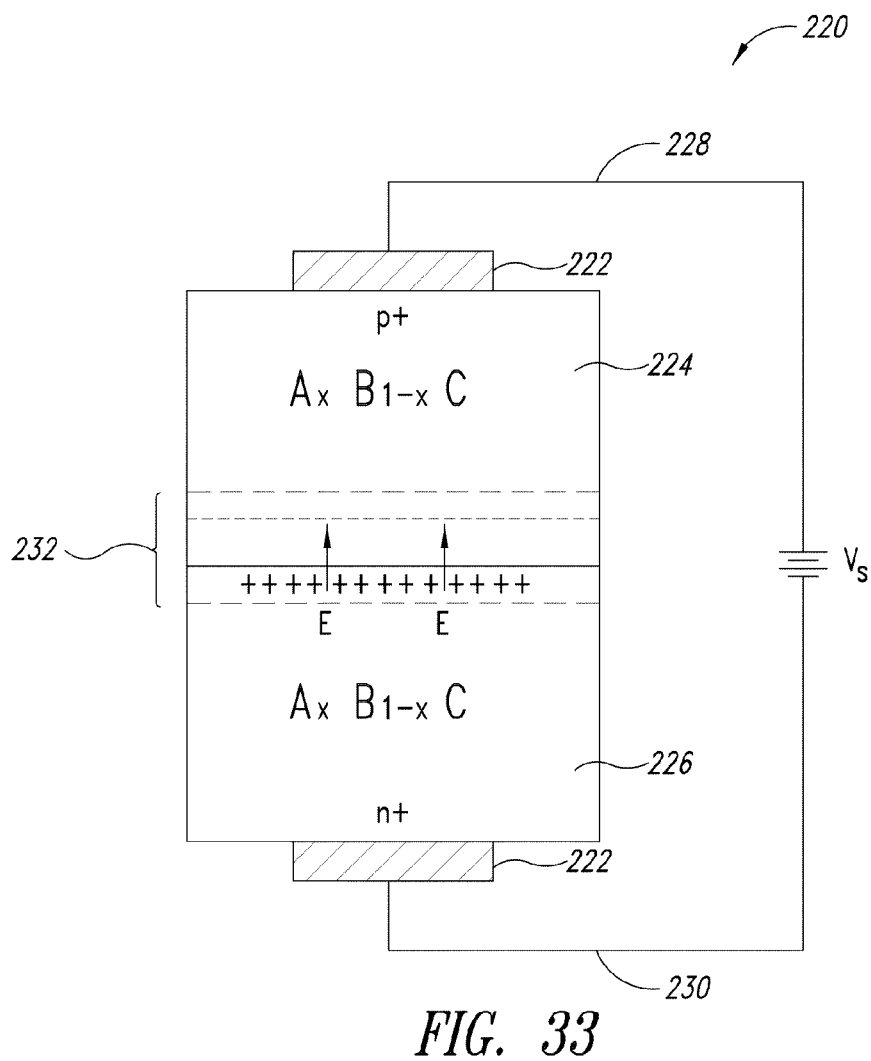
FIG. 33 is a schematic diagram of an LED made according to one embodiment.
Figure 34:
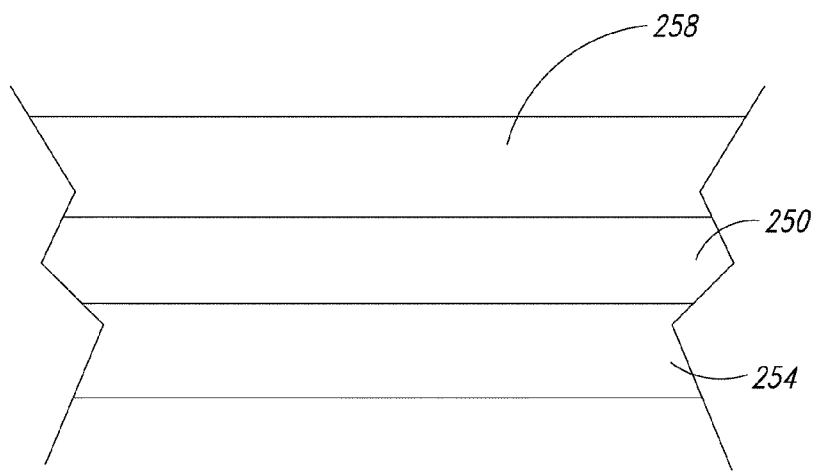
FIG. 34 illustrates schematically an intermetallic structure according to one embodiment.

According to principles discussed herein, the color of the light can be specifically engineered to be a desired wavelength. FIG. 33 illustrates an LED 220 constructed according to embodiments disclosed herein. The LED includes a light emitting material formed of a digital alloy. More specifically, the LED comprises an anode at a first semiconductor region 224 (e.g., formed of a tertiary alloy $A_xB_{1-x}C$) and a cathode at a second semiconductor region 226 (e.g., $A_xB_{1-x}C$) having a junction 232 therebetween. Respective electrodes 222 are coupled to the ends of the diodes which are connected by wires 228 and 230 to a power source Vs. When power is supplied across the depletion region 232 at the junction 232, light is emitted from the diode according to principles well known for light-emitting diodes. By selecting the composition of the nanocrystals and their respective ratio, the semiconductor alloy $A_xB_{1-x}C$ can attain tunable bandgaps, which correspond to emissions at different wavelength.

Currently, different colors are achieved by making changes in the semiconductor composition of the chip. http://www.olympusmicro.com/primer/lightandcolor/ledsintro.html. For example, "[d]epending on the alloy composition, III-nitride devices achieve band gaps ranging from 1.9 eV indium nitride to 3.4 eV gallium nitride (GaN) to 6.2 eV aluminum nitride. The emission wavelengths . . . vary from violet to green (390 to 520 nm) as a function of the indium content in the InGaN active layers." http://oemagazine.com/fromTheMagazine/jul01/ondisplay.html "Color of the light depends on the chemical composition of the semiconductor chip Smaller atoms that lead to higher energy and shorter wavelength light often have zinc blend or wurtzite crystal structure, derived from the diamond structure. Some common compositions: $GaAs_xP_{1-x}$ $Ga_xIn_{1-x}P$ $Al_xIn_{1-x}P$ $Al_xGa_yIn_zP$ $Ga_xIn_{1-x}N$. Atoms with subscripts can substitute for one another in the original structure allowing the color of the emitted light to be tuned". http://mrsec.wisc.edu/Edetc/IPSE/educators/leds.html.

It is very difficult to achieve precise control of the semiconductor composition in vapor deposition, thus necessitating the use of expensive binning and inventory techniques by LED manufacturers. "LEDs have a wide spread in intensity and color. This is true even for one single production batch. Therefore, binning is a must." http://www.chml.com/led_laboratory.php.

By judicious choice of templates, LEDs manufactured with digital alloys in accordance to the description herein can have a tighter color distribution. It is possible to control precisely the composition of a mixture of templates since they can be mixed accurately in solution. It is also possible to fix the digital alloy composition precisely by designing the templates to comprise the desired ratio of appropriate peptide sequences which eliminates the need for mixing two or more different types of templates together. Further, the digital alloy is made at room temperature in solutions held in glass containers, greatly reducing the cost.

Examples of various LED applications can be found at:
http://mrsec.wisc.edu/Edetc/IPSE/educators/leds.html
http://www.ieee.li/pdf/viewgraphs_lighting.pdf
http://spiedl.aip.org/getabs/servlet/GetabsServlet?prog=normal&id=PSISDG005941000001594112000001&idtype=cvips&gifs=yes
http://www.lumileds.com/pdfs/techpaperspres/presentation_SAE%20 2004_kern.PDF
http://www.transporteon.com/Superlatives-L/LED.php
http://www.everlight.com/en_NewsDetail.asp?newsID=200407001
http://www.nichia.com/product/phosphors.html and http://www.mt-berlin.com/frames_cryst/descriptions/led_phosphors.htm
http://www.electrochem.org/publications/jes/samples/JES-H47_1.pdf 4. Intermetallic Layer In addition to tailoring electronic and optical properties, it can also be advantageous to use digital alloys to improve the mechanical performance of materials. As an example, the composition of interconnection materials plays a significant role in the mechanical strength of the interconnect. When the composition at the interconnect interface is optimized, particular intermetallic morphologies are formed which improve the bond strength of the interconnect and which can also improve the diffusion characteristics for better long-term stability. Conversely, if the composition at the interface is not well controlled, a brittle intermetallic phase can form which will lead to an interconnection with low bonding strength. (See, e.g., Wu, et al., J. Elect. Matls., Vol. 34, No. 11, p. 1385; Lee and Subramanian, J. Elect. Matls., Vol. 34, No. 11, p. 1399; Tai, et al., J. Elect. Matls., Vol. 34, No. 11, p. 1357)

FIG. 20 shows an intermetallic layer 250 forming an interface between a first conductive layer 254 and a second conductive layer 258. In one embodiment, the intermetallic layer is based on a digital alloy, as described herein. The formation of such an intermetallic layer allows for a precision control of the composition and location of a mixture of metal nanoparticles at the interface, which provides a method of controlling the metallic composition and morphology of the interconnect for improved interconnection properties.

Since nanoparticles have lower melting temperatures than the corresponding bulk material, intermetallic formation can occur at lower processing temperatures. The incorporation of nanoparticles with the appropriate composition that are localized appropriately within the microstructure of the interconnection can also improve the long-term stability of the interconnect bond through stress relief and prevention of dislocations at the grain boundaries.

As a particular example, an AuIn intermetallic layer at the solder/pad interface acts as a diffusion barrier and prohibited the formation of a brittle Au intermetallic phase. (See, e.g. Wu, et al, J. Elect. Matls., Vol. 34, No. 11, p. 1385; Lee and Subramanian, J. Elect. Matls., Vol. 34, No. 11, p. 1399; and Tai, et al, J. Elect. Matls., Vol. 34, No. 11, p. 1357.) The cost of In prevents its widespread use as a major component in lead-free solder. According to the method described herein, it is possible to localize a higher In concentration at the interface to form the intermetallic interfacial layer. The morphology of the intermetallic has a direct impact on bonding strength, and the formation of column-shaped $(Cu_{0.74}Ni_{0.26})_6(Sn_{0.92}In_{0.08})_5$ intermetallic compounds leads to better bond strengths. These compounds were conventionally formed by, for example, annealing for 500 h at 150° C. According to the method described herein, the intermetallic compound could be advantageously formed directly from nanoparticles of $Cu_{0.74}Ni_{0.26}$ and $Sn_{0.92}In_{0.08}$ that are localized appropriately with a template, especially since the bond strength goes down under lower temperature aging conditions when a different intermetallic morphology is formed.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A light emitting device for emitting light having a wavelength, comprising:
 a substrate layer;
 a first injection contact positioned over the substrate layer;
 a first dielectric layer positioned over the first injection contact;
 a light emission layer positioned over the first dielectric layer, the light emission layer including a nanoparticle layer, wherein the nanoparticle layer comprises a plurality of templates, each template comprising at least one first binding site and at least one second binding site, the first binding site having a specific binding affinity for a first nanoparticle of a first material, the second binding site having a specific binding affinity for a second nanoparticle of a second material, wherein the templates are selected to include, in percentages, x first binding sites and y second binding sites; a plurality of the first nanoparticles bound to respective first binding sites; a plurality of the second nanoparticles bound to respective second binding sites; wherein the templates are assembled such that the first material and the second material form an alloy at a stoichiometric ratio of x:y, and wherein each template is a biological template, which is a biological scaffold fused with the first peptide sequence and the second peptide sequence;
 a second dielectric layer positioned over the light emission layer; and
 a second injection contact positioned over the second dielectric layer.

2. The light emitting device of claim 1 wherein the first material is a compound represented by $A_mB_n$, the second material is a compound represented by $C_pD_q$ and the alloy can be represented by $(A_mB_n)_x(C_pD_q)_y$, wherein,
 A, B, C and D are elements of the Periodic Table;
 $0 \leq m \leq 1$; $0 \leq n \leq 1$; $m+n=1$; and
 $0 \leq p \leq 1$; $0 \leq q \leq 1$; and $p+q=1$, provided that m and n are not 0 at the same time, and p and q are not 0 at the same time.

3. The light emitting device of claim 2 wherein A, B, C, D are different elements, and the alloy is a quaternary alloy.

4. The light emitting device of claim 2 wherein A, B and C are different element, D is the same as B, and the alloy is a ternary alloy.

5. The light emitting device of claim 2 wherein n=q=0, and the alloy is a binary alloy.

6. The light emitting device of claim 2 wherein A, B, C and D are semiconductor elements.

7. The light emitting device of claim 6 wherein A and C are each independently a Group IIIA element, and B and D are each independently a Group VA element.

8. The light emitting device of claim 7 wherein the alloys is $Ga_xIn_{1-x}As_yP_{1-y}$.

9. The light emitting device of claim 7 wherein the alloy is $Ga_xIn_{1-x}N$, $Ga_xIn_{1-x}P$ or $Al_xIn_{1-x}P$.

10. The light emitting device of claim 2 wherein A and C are each a Group IIB element, B and D are each a Group VIA element.

11. The light emitting device of claim 2 wherein A, B, C and D are each independently a metallic element.

12. The light emitting device of claim 1 wherein the first binding site is a first peptide sequence, and the second binding site is a second peptide sequence.

13. The light emitting device of claim 12 wherein the template is engineered such that the first binding sites and the second binding sites are distributed on the template at controllable number and distance from each other.

14. The light emitting device of claim 1 wherein the template is a protein, and the first peptide sequence and the second peptide sequence are portions of the primary structure of the protein.

15. The light emitting device of claim 14 wherein the protein is a chaperonin or a genetically engineered or chemically modified variant thereof, a S-layer protein or a genetically engineered or chemically modified variant thereof, or an apoferritin or a genetically engineered or chemically modified variant thereof.

16. The light emitting device of claim 1 wherein the biological scaffold is a viral particle, a bacteriophage, an amyloid fiber or a capsid.

17. The light emitting device of claim 1, wherein the nanoparticles have pitches in a range of 1-100 nm.

18. The light emitting device of claim 1, wherein the x first binding sites have a first pitch and the y binding sites have a second pitch.

19. The light emitting device of claim 18, wherein the wavelength of emitted light depends upon a ratio of the x first binding sites to the y second binding sites.

20. The light emitting device of claim 1, wherein the first injection contact is an anode for injecting holes into the light emission layer and the second injection contact is a cathode for injecting electrons into the light emission layer.

21. The light emitting device of claim 20, wherein the first dielectric layer has a first thickness selected from a range of 1 to 500 nanometers to facilitate quantum-tunneling of electrons from the cathode to the nanoparticles.

22. The light emitting device of claim 20, wherein the second dielectric layer has a second thickness selected from a range of 1 to 500 nanometers to facilitate quantum-tunneling of holes from the anode to the nanoparticles.

23. A light emitting device for emitting light having a wavelength, comprising:
a substrate layer;
a first injection contact positioned over the substrate layer;
a first dielectric layer positioned over the first injection contact;
a light emission layer positioned over the first dielectric layer, the light emission layer including a nanoparticle layer, wherein the nanoparticle layer comprises a plurality of templates, wherein the templates comprise a first type of templates and a second type of templates, the first type of templates having only the first binding sites, and the second type of templates having only the second binding sites, the first binding site having a specific binding affinity for a first nanoparticle of a first material, the second binding site having a specific binding affinity for a second nanoparticle of a second material, wherein the templates are selected to include, in percentages, x first binding sites and y second binding sites; a plurality of the first nanoparticles bound to respective first binding sites; a plurality of the second nanoparticles bound to respective second binding sites; wherein the templates are assembled such that the first material and the second material form an alloy at a stoichiometric ratio of x:y;
a second dielectric layer positioned over the light emission layer; and
a second injection contact positioned over the second dielectric layer.

24. The light emitting device of claim 23 wherein the first material is a compound represented by $A_mB_n$, the second material is a compound represented by $C_pD_q$ and the alloy can be represented by $(A_mB_n)_x(C_pD_q)_y$, wherein,
A, B, C and D are elements of the Periodic Table;
$0 \leq m \leq 1$; $0 \leq n \leq 1$; m+n=1; and
$0 \leq p \leq 1$; $0 \leq q \leq 1$; and p+q=1, provided that m and n are not 0 at the same time, and p and q are not 0 at the same time.

25. The light emitting device of claim 24 wherein A, B, C, D are different elements, and the alloy is a quaternary alloy.

26. The light emitting device of claim 24 wherein A, B and C are different element, D is the same as B, and the alloy is a ternary alloy.

27. The light emitting device of claim 24 wherein n=q=0, and the alloy is a binary alloy.

28. The light emitting device of claim 24 wherein A, B, C and D are semiconductor elements.

29. The light emitting device of claim 28 wherein A and C are each independently a Group IIIA element, and B and D are each independently a Group VA element.

30. The light emitting device of claim 29 wherein the alloys is $Ga_xIn_{1-x}As_yP_{1-y}$.

31. The light emitting device of claim 29 wherein the alloy is $Ga_xIn_{1-x}N$, $Ga_xIn_{1-x}P$ or $Al_xIn_{1-x}P$.

32. The light emitting device of claim 24 wherein A and C are each a Group IIB element, B and D are each a Group VIA element.

33. The light emitting device of claim 24 wherein A, B, C and D are each independently a metallic element.

34. The light emitting device of claim 23 wherein the templates are biological templates.

35. The light emitting device of claim 23 wherein the first binding site is a first peptide sequence, and the second binding site is a second peptide sequence.

36. The light emitting device of claim 35 wherein the templates are engineered such that the first binding sites and the second binding sites are distributed on the template at controllable number and distance from each other.

37. The light emitting device of claim 23 wherein the templates are proteins, and the first peptide sequence and the second peptide sequence are portions of the primary structure of the proteins.

38. The light emitting device of claim 37 wherein each protein is a chaperonin or a genetically engineered or chemically modified variant thereof, a S-layer protein or a genetically engineered or chemically modified variant thereof, or an apoferritin or a genetically engineered or chemically modified variant thereof.

39. The light emitting device of claim 23 wherein templates are biological scaffolds fused with the first peptide sequence or the second peptide sequence.

40. The light emitting device of claim 39 wherein each biological scaffold is a viral particle, a bacteriophage, an amyloid fiber or a capsid.

41. The light emitting device of claim 23, wherein the nanoparticles have pitches in a range of 1-100 nm.

42. The light emitting device of claim 23, wherein the x first binding sites have a first pitch and the y binding sites have a second pitch.

43. The light emitting device of claim 42, wherein the wavelength of emitted light depends upon a ratio of the x first binding sites to the y second binding sites.

44. The light emitting device of claim 23, wherein the first injection contact is an anode for injecting holes into the light emission layer and the second injection contact is a cathode for injecting electrons into the light emission layer.

45. The light emitting device of claim 44, wherein the first dielectric layer has a first thickness selected from a range of 1 to 500 nanometers to facilitate quantum-tunneling of electrons from the cathode to the nanoparticles.

46. The light emitting device of claim 44, wherein the second dielectric layer has a second thickness selected from a range of 1 to 500 nanometers to facilitate quantum-tunneling of holes from the anode to the nanoparticles.

* * * * *

UNITED STATES PATENT AND TRADEMARK OFFICE
CERTIFICATE OF CORRECTION

| | | |
|---|---|---|
| PATENT NO. | : 7,960,721 B2 | Page 1 of 1 |
| APPLICATION NO. | : 12/030752 | |
| DATED | : June 14, 2011 | |
| INVENTOR(S) | : Angela Belcher et al. | |

It is certified that error appears in the above-identified patent and that said Letters Patent is hereby corrected as shown below:

Column 45, Line 25:
"a first injection contact positioned over the substrate laver;" should read, --a first injection contact positioned over the substrate layer;--.

Column 47, Line 36:
"dielectric laver." should read, --dielectric layer.--.

Signed and Sealed this

Seventh Day of February, 2012

David J. Kappos
*Director of the United States Patent and Trademark Office*